US008381124B2

(12) United States Patent
Martin et al.

(10) Patent No.: US 8,381,124 B2
(45) Date of Patent: Feb. 19, 2013

(54) SINGLE SELECT CLINICAL INFORMATICS

(75) Inventors: Neil A. Martin, Encino, CA (US); Farzad D. Buxey, Marina Del Rey, CA (US)

(73) Assignee: The Regents of the University of California, Oakland, CA (US)

( * ) Notice: Subject to any disclaimer, the term of this patent is extended or adjusted under 35 U.S.C. 154(b) by 440 days.

(21) Appl. No.: 12/509,989

(22) Filed: Jul. 27, 2009

(65) Prior Publication Data

US 2010/0083164 A1 Apr. 1, 2010

Related U.S. Application Data

(60) Provisional application No. 61/137,521, filed on Jul. 30, 2008, provisional application No. 61/085,080, filed on Jul. 31, 2008, provisional application No. 61/085,664, filed on Aug. 1, 2008.

(51) Int. Cl.
*G06F 3/048* (2006.01)
*G06F 3/00* (2006.01)

(52) U.S. Cl. ........ 715/792; 715/803; 715/781; 715/789; 715/802

(58) Field of Classification Search .................... 715/781
See application file for complete search history.

(56) References Cited

U.S. PATENT DOCUMENTS

| | | | | |
|---|---|---|---|---|
| 5,553,609 | A | * | 9/1996 | Chen et al. ..................... 600/301 |
| 5,823,948 | A | * | 10/1998 | Ross et al. ..................... 600/300 |
| 5,867,821 | A | * | 2/1999 | Ballantyne et al. ............... 705/2 |
| 5,924,074 | A | * | 7/1999 | Evans ............................... 705/3 |
| 5,950,002 | A | * | 9/1999 | Hoford et al. ................. 717/109 |
| 5,960,403 | A | * | 9/1999 | Brown ............................... 705/2 |
| 6,049,794 | A | * | 4/2000 | Jacobs et al. ..................... 706/45 |
| 6,246,992 | B1 | * | 6/2001 | Brown ............................... 705/2 |
| 6,283,761 | B1 | * | 9/2001 | Joao ............................... 434/236 |
| 6,519,601 | B1 | * | 2/2003 | Bosch ................................. 1/1 |
| 6,611,846 | B1 | * | 8/2003 | Stoodley ...................... 707/740 |
| 6,674,449 | B1 | | 1/2004 | Banks et al. |
| 6,801,227 | B2 | * | 10/2004 | Bocionek et al. ............. 715/777 |
| 6,832,263 | B2 | * | 12/2004 | Polizzi et al. ................. 709/246 |

(Continued)

FOREIGN PATENT DOCUMENTS

| EP | 1630666 A2 | 3/2006 |
|---|---|---|
| EP | 1865458 A1 | 12/2007 |

(Continued)

OTHER PUBLICATIONS

Oracle Inc. et al. "Absolute Positioning, Java Tutorial" pp. 1-3; 1995 http://docs.oracle.com.*

(Continued)

*Primary Examiner* — Steven B Theriault
(74) *Attorney, Agent, or Firm* — St. Onge Steward Johnston & Reens LLC

(57) ABSTRACT

Some embodiments of the invention provide a single-select method and system for launching clinical information in multiple dashboards based on a selection of a single piece of clinical information (e.g., based on a cursor-click selection of a patient name in a patient list). In some embodiments, each launched dashboard is a single "flat" dashboard that cannot be "drilled down" to another dashboard. In other embodiments, each launched dashboard can be a drilldown dashboard, i.e., a dashboard that is several dashboards that are linked together so that a user can navigate between them by selecting items displayed in the dashboards (e.g., by traversing from a first dashboard to a second dashboard through a selection of an item in a window pane of the first dashboard). Accordingly, some embodiments use the single-select method of some embodiments in lieu of drill-down dashboards, while other embodiments use the single-select method in conjunction with drill-down dashboards.

18 Claims, 21 Drawing Sheets

U.S. PATENT DOCUMENTS

| | | | |
|---|---|---|---|
| 7,165,221 B2* | 1/2007 | Monteleone et al. | 715/738 |
| 7,286,997 B2* | 10/2007 | Spector et al. | 705/2 |
| 7,424,679 B1* | 9/2008 | Lamer et al. | 715/737 |
| 7,480,659 B2* | 1/2009 | Chmura et al. | 1/1 |
| 7,503,010 B2* | 3/2009 | Chaudhri et al. | 715/764 |
| 7,523,401 B1 | 4/2009 | Aldridge | 715/760 |
| 7,548,909 B2* | 6/2009 | Rappaport et al. | 1/1 |
| 7,702,524 B1* | 4/2010 | Whibbs et al. | 705/2 |
| 7,716,149 B2* | 5/2010 | Ducheneaut et al. | 706/45 |
| 7,756,723 B2* | 7/2010 | Rosow et al. | 705/2 |
| 7,792,784 B2* | 9/2010 | Gupta | 707/602 |
| 7,793,232 B2* | 9/2010 | Chaudhri et al. | 715/802 |
| 7,836,403 B2* | 11/2010 | Viswanathan et al. | 715/745 |
| 7,890,517 B2* | 2/2011 | Angelo et al. | 707/752 |
| 7,899,683 B2* | 3/2011 | Schoenberg et al. | 705/2 |
| 7,925,603 B1* | 4/2011 | Laidig et al. | 706/45 |
| 7,952,985 B2* | 5/2011 | Suwabe et al. | 369/275.4 |
| 7,954,064 B2* | 5/2011 | Forstall et al. | 715/779 |
| 7,987,428 B2* | 7/2011 | Handy et al. | 715/762 |
| 8,000,979 B2* | 8/2011 | Blom | 705/2 |
| 2001/0050610 A1* | 12/2001 | Gelston | 340/5.53 |
| 2002/0099678 A1* | 7/2002 | Albright et al. | 706/45 |
| 2002/0152098 A1* | 10/2002 | Evans et al. | 705/4 |
| 2002/0194029 A1* | 12/2002 | Guan et al. | 705/3 |
| 2002/0194090 A1* | 12/2002 | Gagnon et al. | 705/27 |
| 2003/0011646 A1* | 1/2003 | Levine et al. | 345/848 |
| 2003/0125962 A1* | 7/2003 | Holliday et al. | 705/1 |
| 2003/0140044 A1* | 7/2003 | Mok et al. | 707/10 |
| 2004/0024616 A1* | 2/2004 | Spector et al. | 705/2 |
| 2004/0102683 A1* | 5/2004 | Khanuja et al. | 600/300 |
| 2004/0186746 A1* | 9/2004 | Angst et al. | 705/3 |
| 2004/0199543 A1* | 10/2004 | Braud et al. | 707/104.1 |
| 2004/0204963 A1* | 10/2004 | Klueh et al. | 705/2 |
| 2005/0010441 A1* | 1/2005 | Wheeler | 705/2 |
| 2005/0049910 A1* | 3/2005 | Lancaster et al. | 705/10 |
| 2005/0060193 A1* | 3/2005 | Lancaster et al. | 705/2 |
| 2005/0144563 A1* | 6/2005 | Hough et al. | 715/753 |
| 2005/0149852 A1* | 7/2005 | Bleicher et al. | 715/501.1 |
| 2006/0036595 A1* | 2/2006 | Gilfix et al. | 707/5 |
| 2006/0064020 A1* | 3/2006 | Burnes et al. | 600/481 |
| 2006/0085223 A1* | 4/2006 | Anderson et al. | 705/2 |
| 2006/0109961 A1* | 5/2006 | Mahesh et al. | 379/93.25 |
| 2006/0111941 A1* | 5/2006 | Blom | 705/2 |
| 2006/0126801 A1* | 6/2006 | Laperi et al. | 379/32.01 |
| 2006/0205564 A1* | 9/2006 | Peterson | 482/8 |
| 2006/0265651 A1 | 11/2006 | Buck | |
| 2006/0272652 A1* | 12/2006 | Stocker et al. | 128/898 |
| 2007/0011026 A1* | 1/2007 | Higgins et al. | 705/2 |
| 2007/0033129 A1* | 2/2007 | Coates | 705/36 R |
| 2007/0094046 A1* | 4/2007 | Cobbs et al. | 705/2 |
| 2007/0130541 A1 | 6/2007 | Louch et al. | |
| 2007/0174079 A1* | 7/2007 | Kraus | 705/1 |
| 2007/0185739 A1* | 8/2007 | Ober et al. | 705/3 |
| 2007/0194939 A1* | 8/2007 | Alvarez et al. | 340/573.1 |
| 2007/0276702 A1* | 11/2007 | Dani | 705/3 |
| 2007/0294258 A1* | 12/2007 | Caldwell et al. | 707/10 |
| 2007/0294281 A1 | 12/2007 | Ward et al. | |
| 2008/0034060 A1* | 2/2008 | Fisher, Jr. | 709/218 |
| 2008/0059292 A1* | 3/2008 | Myers et al. | 705/11 |
| 2008/0065422 A1* | 3/2008 | Weber | 705/3 |
| 2008/0065433 A1* | 3/2008 | Rosow et al. | 705/5 |
| 2008/0077945 A1* | 3/2008 | Sethuraman | 719/329 |
| 2008/0091454 A1* | 4/2008 | Fisher, Jr. | 705/1 |
| 2008/0097918 A1* | 4/2008 | Spector et al. | 705/51 |
| 2008/0126945 A1 | 5/2008 | Munkvold et al. | |
| 2008/0163066 A1* | 7/2008 | Gu et al. | 715/738 |
| 2008/0243548 A1* | 10/2008 | Cafer | 705/3 |
| 2008/0243549 A1* | 10/2008 | Woronka et al. | 705/3 |
| 2008/0270183 A1* | 10/2008 | Hawkins et al. | 705/2 |
| 2008/0288286 A1* | 11/2008 | Noreen et al. | 705/2 |
| 2009/0024944 A1* | 1/2009 | Louch et al. | 715/765 |
| 2009/0112630 A1* | 4/2009 | Collins et al. | 705/3 |
| 2009/0119127 A2* | 5/2009 | Rosow et al. | 705/2 |
| 2009/0133020 A1* | 5/2009 | Itoh | 718/100 |
| 2009/0133069 A1* | 5/2009 | Conness et al. | 725/46 |
| 2009/0164250 A1* | 6/2009 | Hamilton et al. | 705/3 |
| 2009/0192823 A1* | 7/2009 | Hawkins et al. | 705/3 |
| 2009/0216556 A1* | 8/2009 | Martin et al. | 705/3 |
| 2009/0217189 A1* | 8/2009 | Martin et al. | 715/772 |
| 2009/0217194 A1* | 8/2009 | Martin et al. | 715/783 |
| 2009/0244832 A1* | 10/2009 | Behar et al. | 361/679.55 |
| 2009/0300511 A1* | 12/2009 | Behar et al. | 715/745 |
| 2010/0057646 A1* | 3/2010 | Martin et al. | 706/11 |
| 2010/0077340 A1* | 3/2010 | French et al. | 715/781 |
| 2010/0083164 A1* | 4/2010 | Martin et al. | 715/781 |
| 2010/0107110 A1* | 4/2010 | Mirza et al. | 715/777 |
| 2010/0131883 A1* | 5/2010 | Linthicum et al. | 715/771 |

FOREIGN PATENT DOCUMENTS

| | | |
|---|---|---|
| JP | 2001034690 A | 2/2001 |
| JP | 2003162586 A | 6/2003 |
| JP | 2007249818 A | 9/2007 |
| JP | 2007325742 A | 12/2007 |

OTHER PUBLICATIONS

Oracle Inc. et al. "How to use Layered Panes, Java Tutorial" pp. 1-9; 1995 http://docs.oracle.com.*

Oracle Inc. et al. "How to use Root Panes, Java Tutorial" pp. 1-9; 1995 http://docs.oracle.com.*

Oracle Inc. et al. "Using top Level Containers" pp. 1-5; 1995 http://docs.oracle.com.*

STIC Multi-level Search Results, Scientific and Technical Information Center, Dec. 3, 2011 results of searching the phrases "Dashboard and Clinical" in the title. pp. 1-3.*

Hansen, et al.; "Moving out of the Lab: Deploying Pervasive Technologies in a Hospital"; Jul.-Sep. 2006; IEEE CS and IEEE ComSoc, Pervasive Computing IEEE vol. 5 Issue 3, pp. 25-26.

* cited by examiner

SINGLE SELECT CLINICAL INFORMATICS

CROSS-REFERENCE TO RELATED APPLICATIONS

The present application claims the benefit under 35 U.S.C. §119(e) of the Provisional Patent Application Ser. No. 61/137,521 entitled "Single Select Clinical Informatics" filed Jul. 30, 2008.

The present application claims the benefit under 35 U.S.C. §119(e) of the Provisional Patent Application Ser. No. 61/085,080 entitled "Single Select Clinical Informatics" filed Jul. 31, 2008.

The present application claims the benefit under 35 U.S.C. §119(e) of the Provisional Patent Application Ser. No. 61/085,664 entitled "Single Select Clinical Informatics" filed Aug. 1, 2008.

The present application is related to co-pending U.S. patent application Ser. No. 12/512,721 entitled "Launching of Multiple Dashboard Sets that Each Correspond to Different Stages of a Multi-Stage Medical Process," filed on Jul. 30, 2009. The application is incorporated herein by reference.

FIELD OF THE INVENTION

The invention is directed towards a clinical information system that provides intelligent dashboards for viewing patient data.

BACKGROUND OF THE INVENTION

In recent years, hospitals have increased the amount of information they produce about each patient in digital form to an extent that would be overwhelming to a human being trying to cope with every bit of that information. For example, a patient's heart rate or blood pressure might be continuously monitored with a new value generated several times a minute.

Accordingly, systems for displaying such data have been developed. Some of these systems take the form of dashboards for computer or other electronic displays for displaying specific information about a patient. Unfortunately, in many cases, the overwhelming amount of raw data has been replaced by an overwhelming number of different options as to which dashboard will provide the most useful information about a patient at any given time. Therefore, a need has arisen for a system that helps a user select an appropriate dashboard to use to display information about a selected patient.

SUMMARY OF THE INVENTION

Accordingly, it is an object of the present invention to provide a system and method for displaying relevant information for both doctors and nurses. It is a further object of the invention to provide a method and device for launching multiple dashboards in response to a single selection of medical data. It is another object of the invention allowing for an element to switch between dashboards, whereby a user can manually switch between dashboards, or such the element provides for automatic scrolling between dashboards. It is another object of the invention to provide for a method for creating a new dashboard, which can be saved, so that the system can be customized based upon the particular needs of a user, such as a doctor or nurse.

These and other objectives are achieved by providing a device for displaying clinical information comprising: an interface having a first display area and a second display area, and one or more dashboards, the one more dashboards each having one or more window panes, wherein a first dashboard is displayed in the first display area, and the remaining dashboards are displayed as selectable icons in the second display area, and wherein the first dashboard and the remaining dashboards can be switched by an element, wherein the element switches the first dashboard displayed in the first display area with a dashboard corresponding to a selectable icon displayed in the second display area.

Some embodiments of the invention provide a single-select method for launching clinical information in multiple dashboards based on a selection of a single piece of clinical information (e.g., based on a cursor-click selection of a patient name in a patient list). In some embodiments, each launched dashboard is a single "flat" dashboard that cannot be "drilled down" to another dashboard. In other embodiments, each launched dashboard can be a drilldown dashboard, i.e., a dashboard that is several dashboards that are linked together so that a user can navigate between them by selecting items displayed in the dashboards (e.g., by traversing from a first dashboard to a second dashboard through a selection of an item in a window pane of the first dashboard). Accordingly, some embodiments use the single-select method of some embodiments in lieu of drill-down dashboards, while other embodiments use the single-select method in conjunction with drill-down dashboards.

The method of some embodiments starts (also referred to as launches or instantiates) multiple dashboards based on the selection of a single piece of clinical information. In some embodiments, one of the launched dashboards is displayed at its full resolution in a first display area of the display device, while the other launched dashboards are displayed as selectable icons (e.g., displayed as selectable thumbnails) in a second display area of the display device (e.g., in a display area below, above or to the side of the first display area, or in a display area overlapping the bottom, the top, the left or the right side of the first display area). Some of these embodiments also display a selectable icon in the second display area for the dashboard that is being displayed in the first display area.

The selection of a selectable icon (e.g., a cursor click on the icon) in the second display area causes the display of the icon's associated dashboard in the first display area. In addition to this selection approach or in lieu of this approach, other embodiments use other techniques to display and navigate through the launched dashboards that are not being viewed at a particular time in the first display area. For instance, in the embodiments that display the dashboards on touch sensitive displays, some embodiments might allow a user to switch between the dashboards (i.e., to change the dashboard being displayed in the first display area) by swiping his hand over the display device in a particular direction (e.g., to the left or to the right). This swiping motion causes the first display area to switch from displaying a particular dashboard to one that is to the side of the particular dashboard that is opposite the direction of the swiping motion.

Given the large number of dashboards that are launched together, some embodiments allow a user (e.g., a doctor or other practitioner, a system administrator, etc.) to customize one or more window panes of a dashboard to display only a particular view of a particular clinical information piece (e.g., a 24 hr graph of glucose level). In some such embodiments, the user can optimize a dashboard to include several such parameter- and view-specific window panes that maximize the amount of data viewable at any given time and/or that group together clinical information views for quick deciphering and correlation by a practitioner. For instance, a left side of a dashboard could show several stack-aligned panes, each showing a vital statistic over a time period, while a right side of dashboard shows several stack-aligned panes, each showing a laboratory measurement over the same or different time period. Such parameter and data intensive dashboard can be printed or e-mailed for providing practitioners detailed snapshots of a patient's condition at a particular time. The use of the parameter and view-specific dashboards is not limited to embodiments that launch multiple dashboards at once.

Because several window panes of a dashboard can be parameter-specific, some embodiments define a data element to represent each parameter that is presented in each parameter-specific window. For instance, assume that a dashboard has three specific window panes showing different views of a particular measurement value. One showing a running twenty-four hour graph of a particular measurement value, one showing the running twenty-four hour graph of the average of the particular measurement value, and one showing the running twenty-four hour graph of the variability coefficient associated with the change of the particular measurement value. Some embodiments would define a different data element to keep track of each of the values displayed in each of these three window panes, even though they all relate from the same measurement value. These embodiments define these data elements so that different mathematical functions and display views can be defined for each of them. The use of the data-element model is not limited to the embodiments that use parameter- and view-specific panes.

Some embodiments provide several software tools to allow a user to design a dashboard. For instance, some tools allow the user to specific the number of panes in a dashboard, to select among different layout types for a particular number of panes, to move and adjust window panes in a dashboard that is from a selected dashboard layout, etc. Some embodiments allow a user to tie a window pane to a particular view of a particular parameter. For instance, in some embodiments, the user can (1) right-hand click on a window pane in a dashboard, (2) select vital signs instead of lab measurements in a menu that is displayed in a resulting menu, (3) select heart rate in a resulting drop down menu of vital sign, and then (4) select a particular view (e.g., running twenty-four hour view) of the heart rate. The software tools of some embodiments allow the user to move and resize the window panes so that the user can create aligned and/or condensed parameter- and view-specific panes in order to maximize the amount of data being viewed and/or to simplify the correlation of such data.

The invention further provides a method for launching clinical information comprising: providing an interface, providing one or more dashboards, displaying a first dashboard in a first display area of the interface, displaying the remaining dashboards as selectable icons in a second display area of the interface, selecting a selectable icon from the second display area, and displaying the dashboard corresponding to the selected selectable icon in the first display area, and displaying the first dashboard as a selectable icon in the second display area.

The present invention may further comprise selecting additional selectable icons to display additional dashboards in the first display area for a multi-stage procedure or operation, wherein the additional selectable icons selected are displayed in the first display area. The selecting step may further comprise an element that allows for a selectable icon from the second display area to be picked. This element may be selected from a group consisting of a touch sensitive element, scrolling element, cursor, switch, automated element, tag, RFID tag, voice control, or wireless device.

The element may allow for automated scrolling of the dashboards, or may allow for manual scrolling of the dashboards. The element may be worn or carried by a user, such as if the user is in close proximity to the system, the dashboards might switch based upon the configuration of the element, which may be based upon the preferences of the user.

The method may further allow for the first dashboard to be displayed as a selectable icon in the second display area. The method may allow for the first dashboard to have a predefined configuration based upon a selected user profile, and may allow for each of the dashboards to have multiple window panes.

The invention further comprises a method for launching clinical information comprising: providing an interface, and one or more dashboards, the one or more dashboards each having one or more window panes; displaying a first dashboard in a first display area of the interface; displaying the remaining dashboards as selectable icons in a second display area of the interface; selecting an item in a window pane of the first dashboard and displaying the corresponding dashboard configured to the item selected in the first display area of the interface. The window pane selected may correspond to a selectable icon and dashboard displayed in the second display area.

This method may further comprise hiding or closing the first dashboard in the first display area and displaying the corresponding dashboard configured to the item selected in the first display area. The corresponding dashboard configured to the item selected may be displayed in a third display area that partially overlaps the first display area. The dashboards may be linked form a multi-stage operation of multiple dashboards.

The invention further involves a method for creating a new dashboard comprising: displaying a dashboard with a first set of window panes; receiving a change request to create a new dashboard by changing the view of one or more window panes of the dashboard; changing the view of one or more window panes of the dashboard to display a second set of views; receiving a set of rules from a user for displaying the new dashboard; displaying the new dashboard; and saving the new dashboard to a database.

The method may further comprise linking the new dashboard to other dashboards, and/or keeping the need dashboard private. The method may involve determining if a user has permission to modify the dashboard.

A dashboard is defined as a collection of window panes that are part of a single display presentation. All the window panes of a dashboard can typically be collectively viewed in a display, although in some embodiments the dashboard (and hence some of its window panes) can extend beyond the boundaries of the display.

The information displayed in a window pane (also referred to as the "view" of a window pane) may be in different forms, including reports, lists, notes, graphs, images, etc. Each window pane can present one or more views of (1) one or more clinical data items (e.g., present a list or graph associated with a vital signal or lab measurement) or (2) established treatment guidelines or protocols (e.g., guidelines from public reference sources or from customized intramural institutional policies regarding particular conditions or measurements).

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The novel features of the invention are set forth in the appended claims. However, for purpose of explanation, several embodiments are set forth in the following figures.

DETAILED DESCRIPTION OF THE INVENTION

Section I below introduces terms and concepts relating to dashboards, window panes, drill-down dashboard, etc. Section II provides an overview of the single-select method for launching of multiple dashboards. Section III then provides more detail regarding the single select method of some embodiments.

I. Overview

A dashboard is a collection of window panes that are part of a single display presentation. All the window panes of a dashboard can be typically collectively viewed in a display, although in some embodiments the dashboard (and hence some of its window panes) can extend beyond the boundaries of the display.

The information displayed in a window pane (also referred to as the view of a window pane) may be in different forms, including reports, lists, notes, graphs, images, etc. Each window pane can present one or more views of (1) one or more clinical data items (e.g., present a list or graph associated with a vital signal or lab measurement) or (2) established treatments guidelines or protocols (e.g., guidelines from public reference sources or from customized intramural institutional policies regarding particular conditions or measurements).

Figure 1:
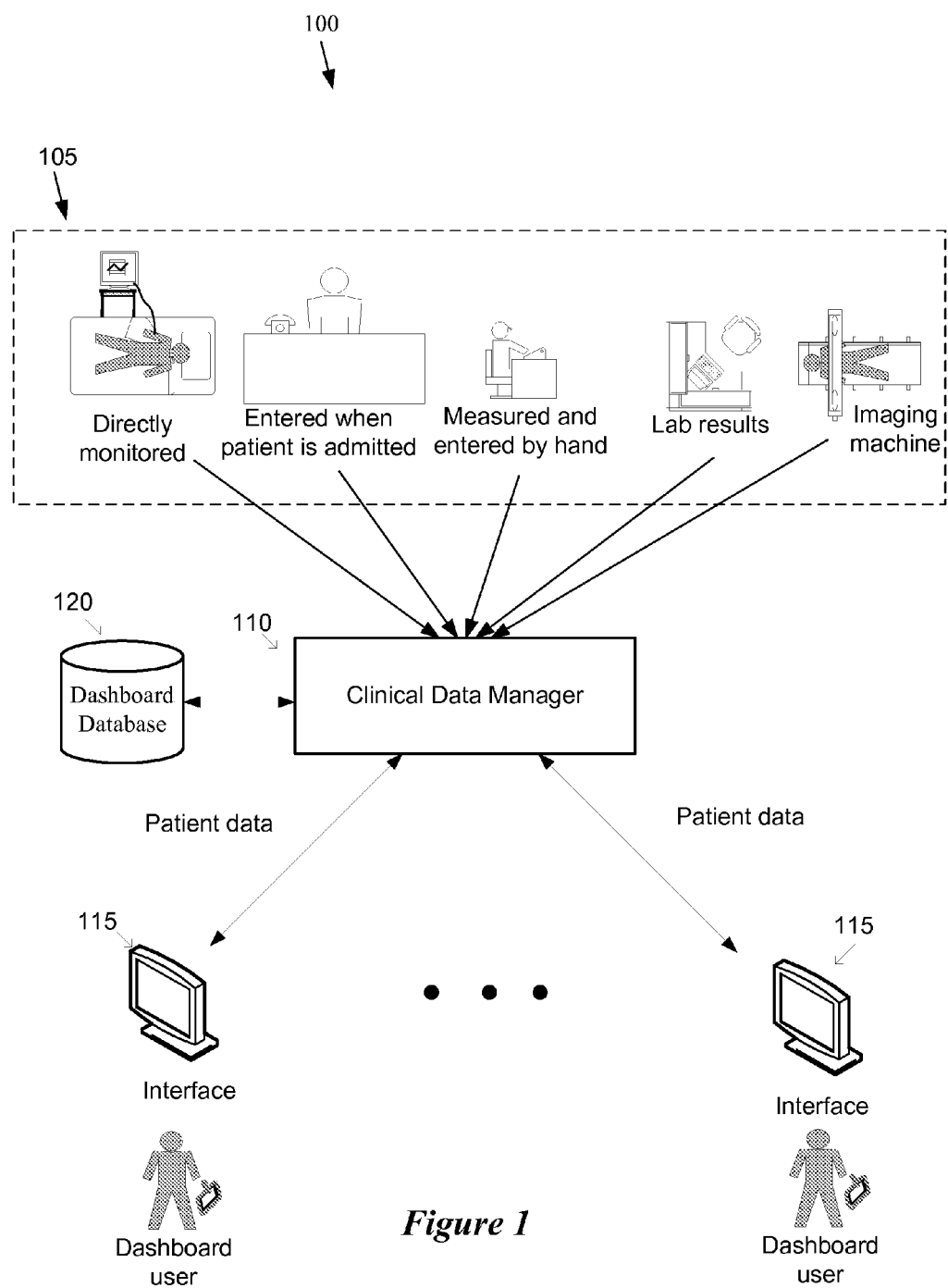
FIG. 1 illustrates a system architecture of some embodiments.

FIG. 1 illustrates a conceptual system architecture of a clinical information system. As shown, patient data is received from several disparate patient data sources 105 at clinical data manager 110. The clinical data manager 110 collects objective data such as vitals from monitors monitoring the patients, lab reports, and medical images (e.g., x-rays, Magnetic Resonance Imaging (MRI), Computed Tomography (CT) scans, etc.), and subjective data such as physicians' assessments, physicians' diagnosis, or physician treatment plans from the various data sources 105. This collection of data may come from one or more locations such as different labs and hospitals.

The clinical data manager 110 receives, normalizes, analyzes, and/or aggregates the patient data for the purposes of gathering data about individual patients (as a snapshot of a patient's data or as a record of the data over time), and/or for the purpose of comparing statistics among patients (in some cases including the change in statistics of each patient) for various reasons, for example, in order to efficiently allocate medical resources.

The clinical data manager 110 reports data, disseminates data, and/or alerts users to data through various clinical information interfaces 115. These interfaces can be different from each other depending on the job of the user within the medical system, or the particular terminal on which the interfaces are displayed, and/or the momentary needs of the individual user and/or patient. In some embodiments, the interfaces are different depending on the location. For example, a user in the cardiac intensive care unit will receive one set of data and a user in neurosurgery will receive a different set of data. As will be further described below, the interface may be different depending on a particular patient's diagnosis or condition. The clinical data manager can also provide the data in real-time to the various interfaces 115.

Figure 2:
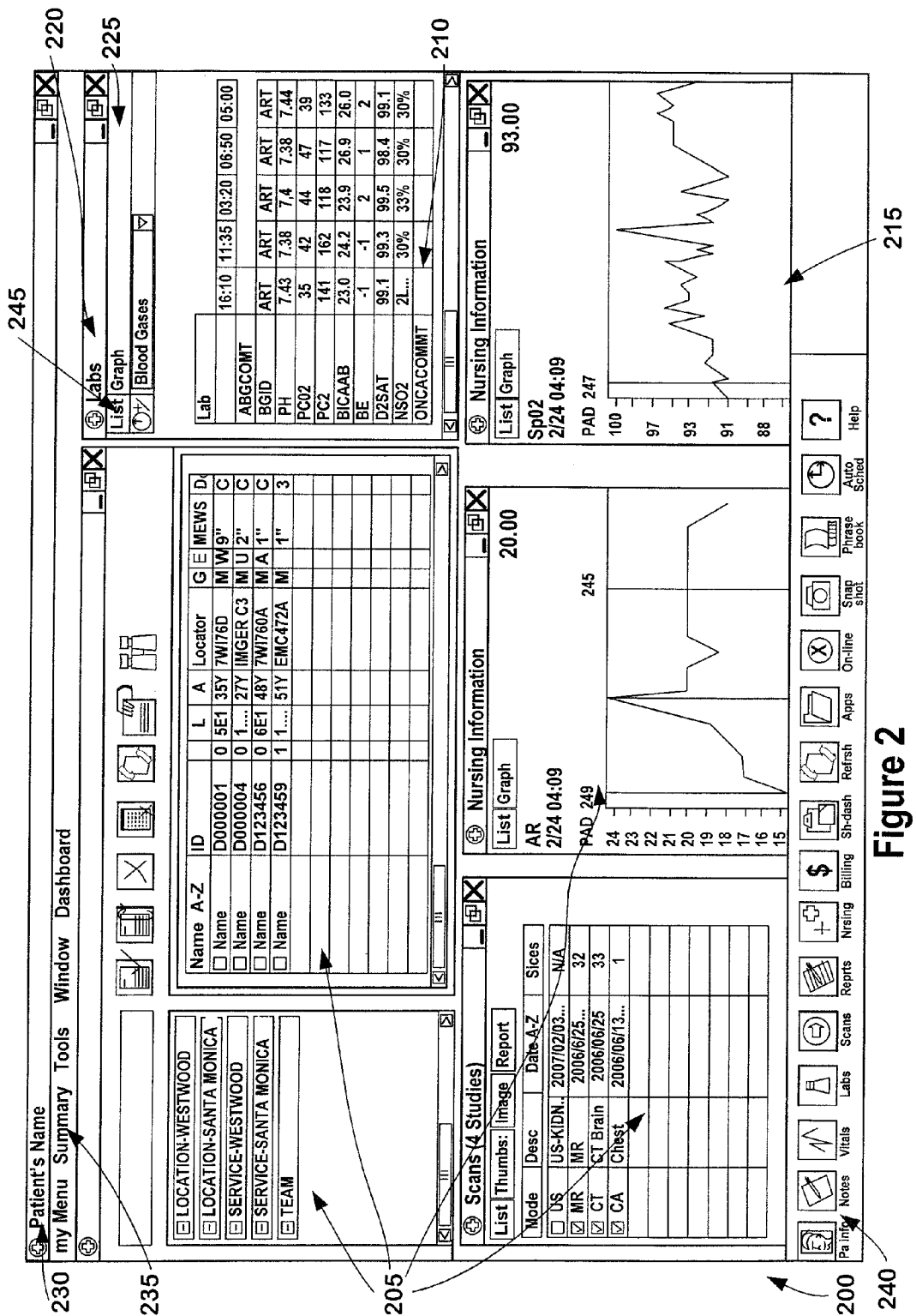
FIG. 2 illustrates an example of a dashboard of some embodiments.

FIG. 2 provides an illustrative example of one such clinical information interface 200. As shown, the interface is provided graphically and includes (1) a title bar 230, (2) a menu bar 235, (3) a master toolbar 240, and (4) several windows 205. The master toolbar 240 appears at the bottom of the interface 200 and contains easy access to different application functionalities. For example, the master toolbar might include a button to refresh the clinical data, view lab results, view billing information, open up other windows, etc.

Several of the windows in the interface 200 display clinical data for one or more patients. The information displayed in a window pane may include reports, lists, notes, graphs, images, etc. For example, the information displayed may include the data needed to assess the severity of the patient's condition, the trend (e.g., improving and deteriorating) of the condition, the cause of the condition, the secondary consequences of the condition, etc. As illustrated, each window 205 can optionally have a title bar 220 that displays information about the window and a menu bar 225 that may include selectable tabs, pull-down menu, search bar, or various other tool buttons.

Several of the window panes present different views of one or more clinical data items. For instance window pane 210 provides a view for displaying a lab report for "blood gasses"

of a patient. The lab report is presented as a list of measurement for several blood gases, and, in some cases, a particular item on the list can be expanded to present additional detail. However, the lab report can also be presented as a graph by selecting the item in the list and selecting a tab 245 in the menu bar 225. The lab report can be presented as a graph by simply selecting the item (e.g., by double clicking the item) in the list. The view provided by the window pane 215 is an example of a graph that depicts the percentage of oxygen saturation in blood (SpO2) of the patient over a period of time. The information that is displayed in the view may include established treatments guidelines, or protocols. Such guidelines may come from public reference sources, or from customized intramural institutional policies. For instance, when a patient is diagnosed with hyperglycemia, one of the views of a dashboard may present a university's policy on how the condition is treated.

The collection of one of more window panes 205-210 is a dashboard. Two or more dashboards can be linked together such that while viewing a first dashboard, a second dashboard can be opened up upon selection of an item in the first dashboard. When the second dashboard is opened, the first dashboard is automatically minimized, hidden or, in some cases, closed. Also, when the second dashboard is opened, the first dashboard can be arranged in a manner so that both dashboards can be viewed concurrently.

The linking of the dashboards can be based on what the user most wants to see. Specifically, the information that is displayed in one or more views of the dashboard is designed and configured with intent to follow the typical train of thought and sequence of assessments of a trained or experienced professional such as a doctor. For example, one dashboard might link to a spreadsheet of ten most relevant lab results over time, or might lead to a trend plot of one or two key lab results over time. This allows the user of the interface to obtain the most relevant information without having to sort through the mass of information.

In addition of the linking of dashboards, the dashboard can be opened up to a predefined configuration. In this way, the user is initially presented with the most relevant information. This concept of initially presenting the most relevant information is also referred to as the drill down concept because it drills through the masses of data and quickly pulls out the data that the user wants to see first. For example, rather than starting with a view containing a list of all radiology scans of a patient, the dashboard may be configured to start with a view of a current chest x-ray and a view of a previous chest x-ray. Therefore, instead of pulling data out by a pull model (e.g., selecting different links to receive the relevant data), the dashboard can utilize a push model that pushes the relevant data out as a first view. The different configurations of the dashboards can be provided and stored in the dashboard library or database 120 as shown in FIG. 1. The relevant data is not only pulled from medical facilities, but is pulled from different servers across the Internet (e.g., library, educational institutions, etc.).

A. Linking of Different Dashboards

Different dashboards can be linked to each other in a hierarchy of dashboards. An initial set of these dashboards can be pre-configured and made available for a user to view clinical information for one or more patients. A user can start from a top level dashboard and activate another dashboard by selecting an item or link in the current dashboard.

Figure 3:
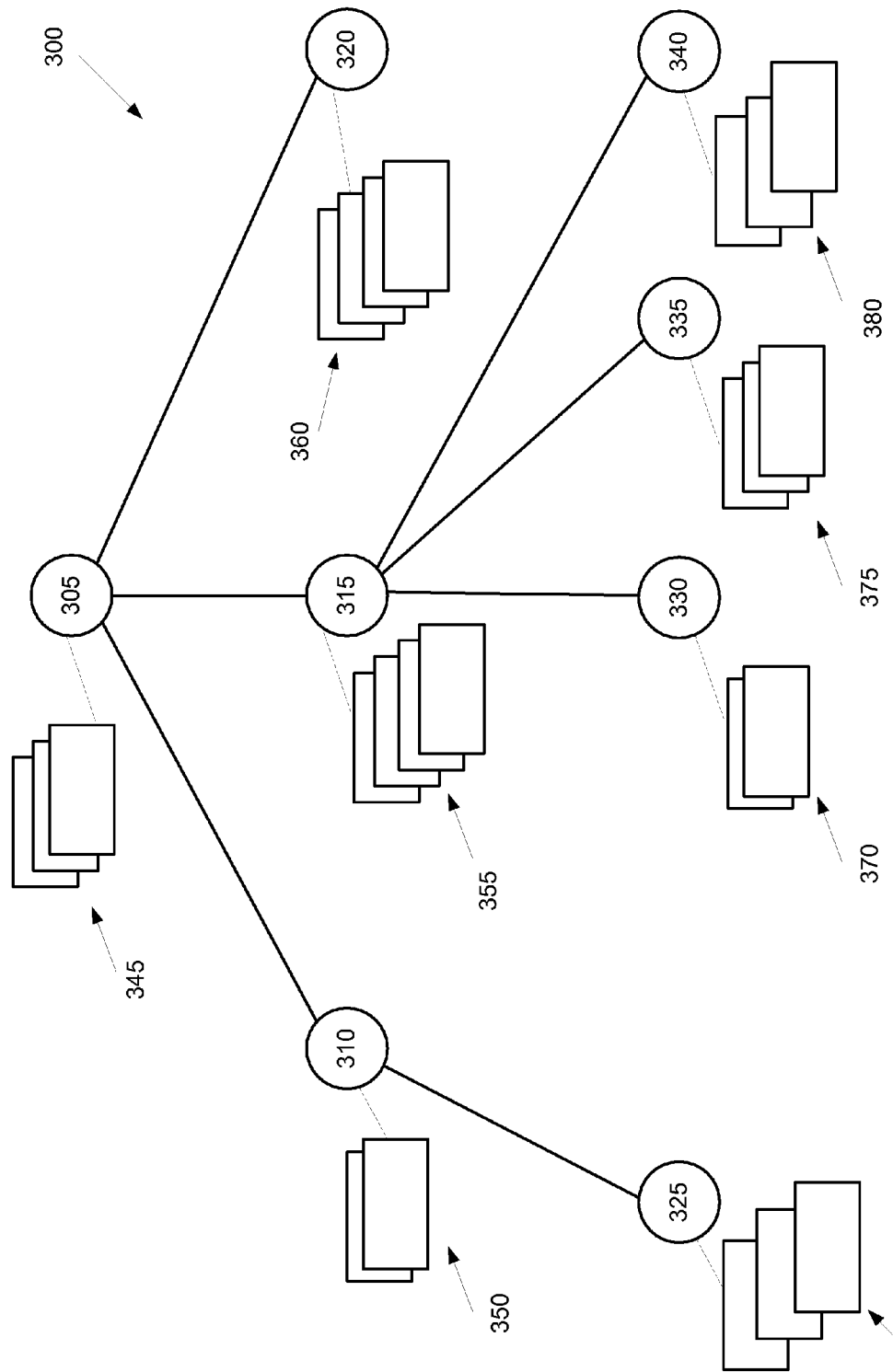
FIG. 3 illustrates a hierarchy of dashboards that provides an example of linking different dashboards together.

FIG. 3 illustrates a hierarchy 300 of dashboards. The figure includes a top level node 305 and several other nodes 310-340. Each node of the hierarchy represents one particular dashboard. Each dashboard has one or more window panes 345-380 associated with it. For instance, dashboard 325 has three windows panes 365. Each window pane provides a specific view for one or more clinical data items. For instance, these windows might show different information for a particular patient. One window pane might show a CT scan of the patient, the other window pane might show a lab report, and the third window might show a graph of oxygen saturation.

Also, as shown in FIG. 3, each dashboard might be linked to one or more other dashboards. For instance, dashboard 315 is linked to three other dashboards 330-340. Each one of these dashboards are activated when an item is selected (e.g., by double clicking on a displayed item in a window pane) in dashboard 315. In some embodiments, the activation or display of another dashboard minimizes, hides, or closes the currently selected dashboard.

The linking of the dashboards can be based on what the user most wants to see. The information that is displayed in one or more views of the dashboard is designed and configured with intent to follow the typical train of thought and sequence of assessments of an experienced or trained professional. This allows the user of the interface to obtain the most relevant data without having to sort through the different collections of data.

Figure 4:
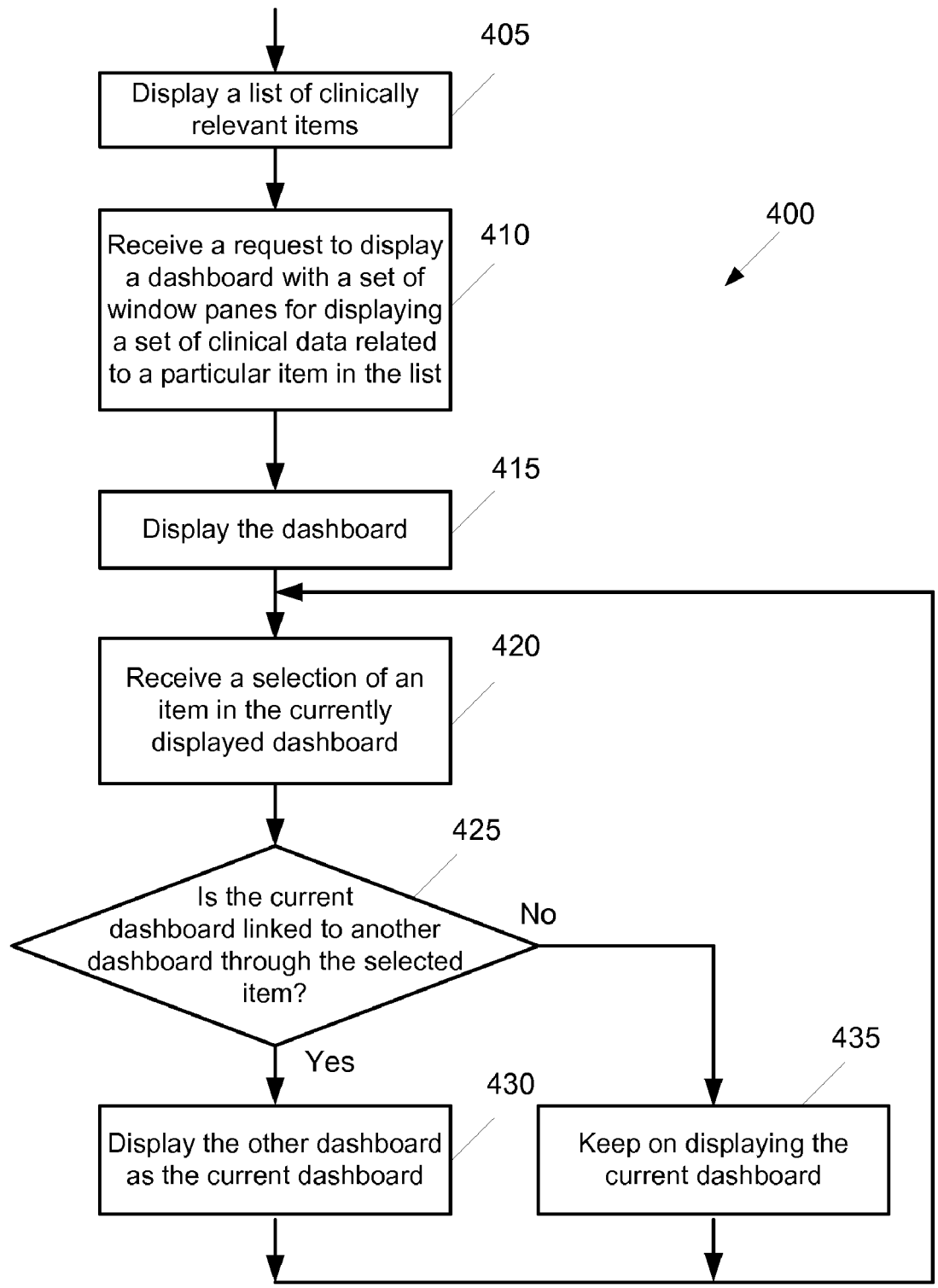
FIG. 4 conceptually illustrates a process for linking different dashboards together in some embodiments.

FIG. 4 conceptually illustrates a process 400 for linking different dashboards together. As shown, the process displays (at 405) a list of clinically relevant data in a clinical information interface. For instance, the process may display a list of different patients in a particular ward in a hospital, a list of all patients of a particular physician, or a list of all patients with a particular disease. In some cases, the process may display a summary window that contains information about one or more patients.

Figure 5:
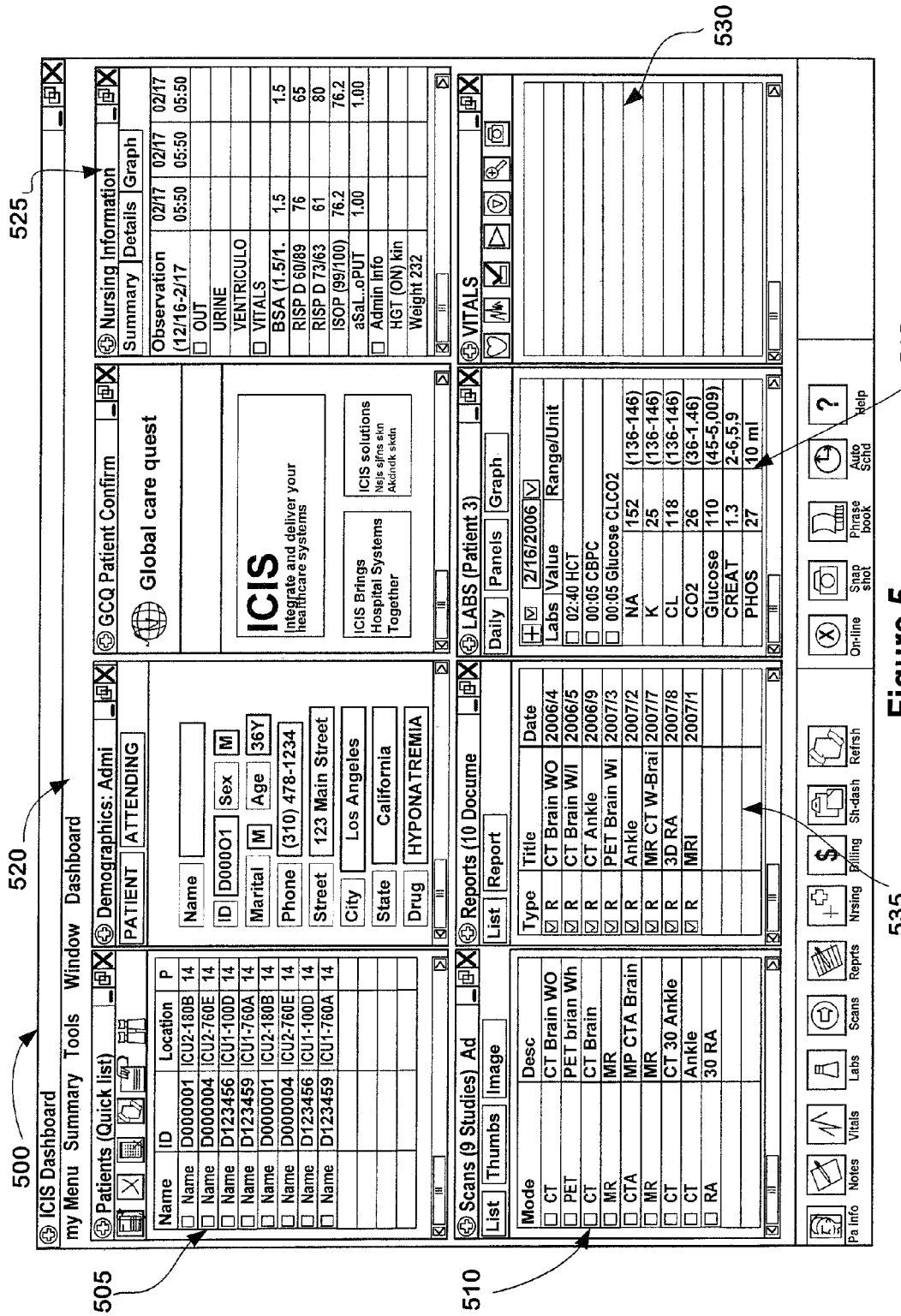
FIG. 5 illustrates example of a dashboard that links to another dashboard.

Next, at 410, the process receives a request for displaying a dashboard with a set of panes for displaying a set of clinical data related to a particular item in the list. For instance, a physician might click on the name of a patient to display data related to that patient. The process then displays (at 415) the dashboard. FIG. 5 provides one such example of a dashboard 500 that is displayed when a patient is selected from a patient list window 505. Specifically, this dashboard displays several window panes that include clinical data for a patient selected from the patient list window 505. Optionally, the patient list window 505 may not be considered part of the dashboard.

As illustrated in FIG. 5, when a user selects a patient from the patient list window, the user is presented with dashboard 500 that includes (1) a scan result window 510 that displays a patient's scan results, (2) lab results 515 window that displays several lab results, (3) demographics window 520 that displays the patient's demographic, (4) nursing information window 525 that displays nursing information, (5) vitals window 530 that displays the patient's vitals, and (6) reports windows 535 that displays the patient's reports.

Next, at 420, the process receives an indication that an item is selected in the dashboard. Referring back to FIG. 3, a dashboard (such as 315) might be linked to several other dashboards 330-340 through different items in the dashboard. When one of those items is selected (e.g., with click on that item), the corresponding dashboard is displayed. For instance, a view of a window may include a link to several recommended dashboards for a particular condition. Optionally, when a particular item is selected (e.g., when a user right-clicks or otherwise selects in some manner), the user is presented with one or more recommended dashboards. Selecting an item can cause an existing view of window pane that shows recommended dashboards to show recommend dashboards related to that selected item. In this way, the user is able to navigate from one dashboard to another dashboard in order to easily view relevant data.

Figure 6:
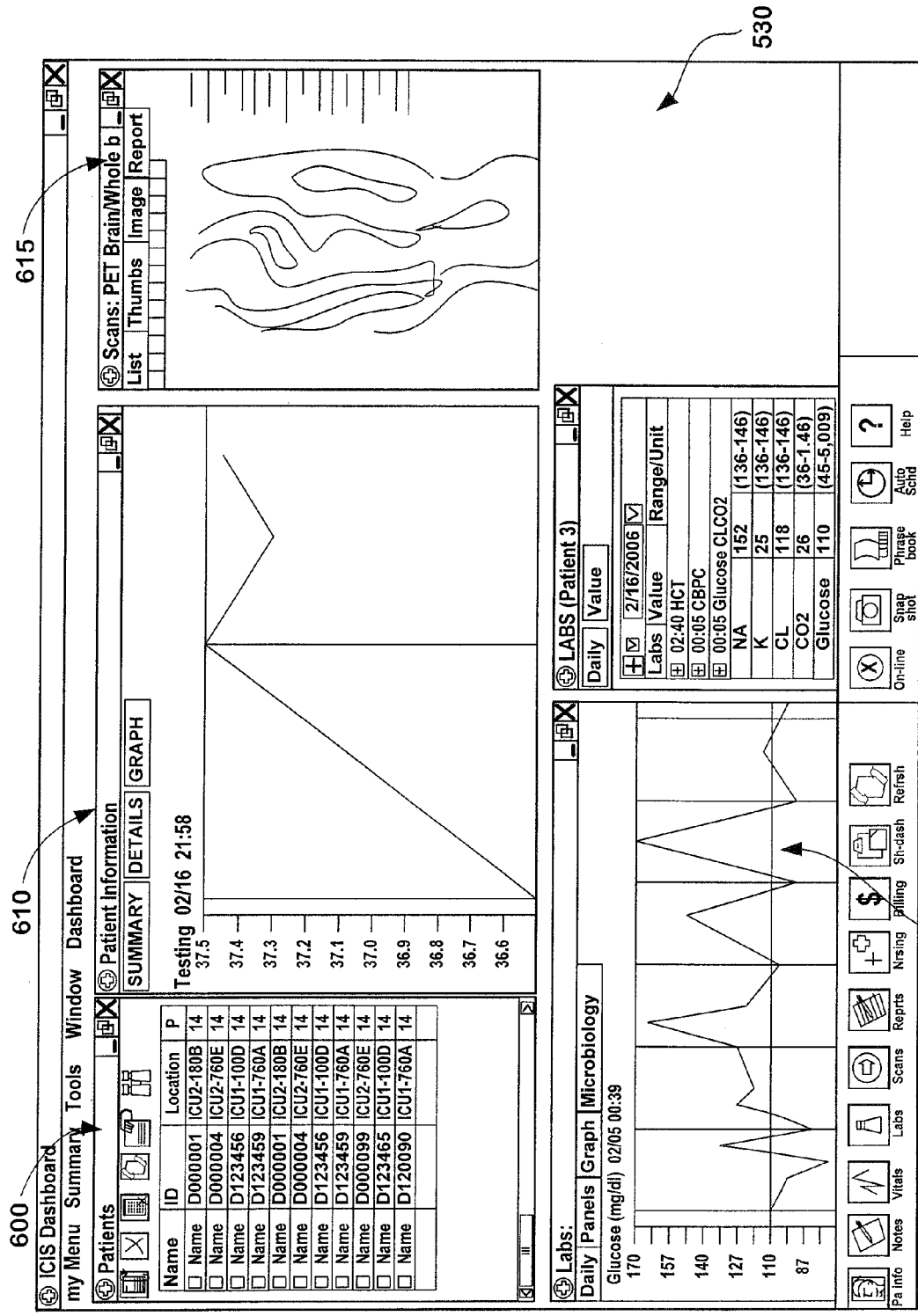
FIG. 6 illustrates an example of a dashboard that is linked to the dashboard as illustrated in FIG. 5.

Therefore, when the process determines (at 425) that the current dashboard is linked to another dashboard through the selected item, the process displays (at 430) the other dashboard. FIG. 6 provides one example of another dashboard 600 which is displayed when an item is selected from dashboard 500. Specifically, the user has selected a link in one of the windows or has selected a recommended dashboard from several recommended dashboards. As illustrated, instead of showing several tables and reports, dashboard 600 presents the user with a dashboard that includes graph of glucose 605, graph of temperature 610, and image view 615 of the patient. In some embodiments, the different dashboards are linked to display situationally appropriate information. For example, a dashboard showing a patient's condition may be linked to another dashboard related to treating that condition.

The process then proceeds to 420 which was described above. On the other hand, when the process determines that the current dashboard is not linked to any other dashboard through the selected item, the process (at 435) keeps on displaying the current dashboard. For instance, if an item in dashboard 500 does not link to any other dashboard (e.g., there are no more data related to this item), the current dashboard remains displayed. After 435, the process proceeds to 420 which was described above.

B. Drilling Down to a Dashboard

One or more dashboards can be opened up to a predefined configuration. In this way, the user is initially presented with the most relevant information. This concept of initially presenting the most relevant information is also referred to as the drill down concept because it drills through the masses of data and quickly pulls out the data that a user wants to see first. For example, rather than starting with a view containing a list of all radiology scans of a patient, the dashboard may be preconfigured to start with a view of a current chest x-ray and a view of a previous chest x-ray. The pulling of the data can occur not only at the patient level but also at the user level. In other words, the role of the user (e.g., doctor, nurse) and the location of the user may also be contributing factors in pulling the relevant data. For instance, a nurse in the cardiac intensive care unit will receive a different set of data than a neurosurgeon.

Figure 7:
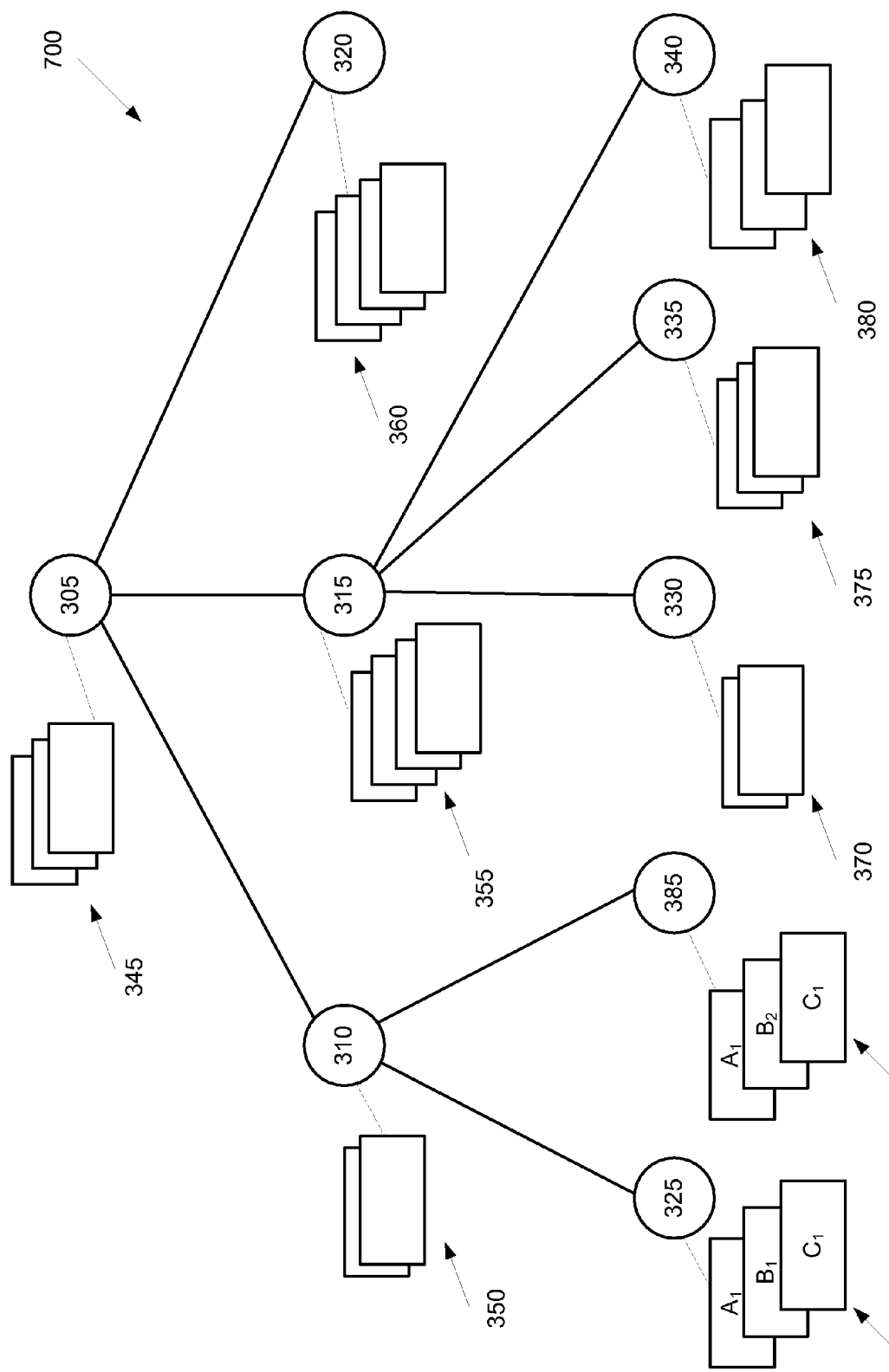
FIG. 7 illustrates a hierarchy of dashboards that provides an example of customizing a view within a window of a dashboard.

FIG. 7 presents a hierarchy 700 of dashboards that illustrate the dashboard customization. The hierarchy has the same dashboards as in FIG. 3 except that a user has created a new dashboard 385 based on an existing dashboard 325. As shown, dashboard 325 has three windows panes with three different views $A_1$, $B_1$, and $C_1$. These window panes may, for example, show a CT scan, a lab report, and a graph of oxygen saturation.

In the example of FIG. 7, the user has determined that for a particular patient instead of showing a full lab report in the second window pane, showing a graph of glucose change is more appropriate. The user can create a new dashboard which is similar to dashboard 325 except that the view in the second window pane is changed from the lab report to the graph for glucose change. The new dashboard 385 has three window panes 390. Two of these panes have the same views $A_1$ and $C_1$ as in dashboard 325. The other window pane, however, has a new view $B_2$ which shows a graph of glucose change. The new dashboard 385 can be saved. This new dashboard is saved in the dashboard database or library 120 as illustrated in FIG. 1. From then on, for this particular patient, dashboard 385 (instead of dashboard 325) is opened from dashboard 310. This configuration can also be saved so that the user can also use dashboard 385 for other patients, instead of dashboard 325. For example, when treating a patient with similar medical condition, instead of a default preconfigured dashboard, the user is presented with the reconfigured dashboard 385. This reconfigured dashboard can be provided automatically or as a selectable option (e.g., menu item, tool button).

Figure 8:
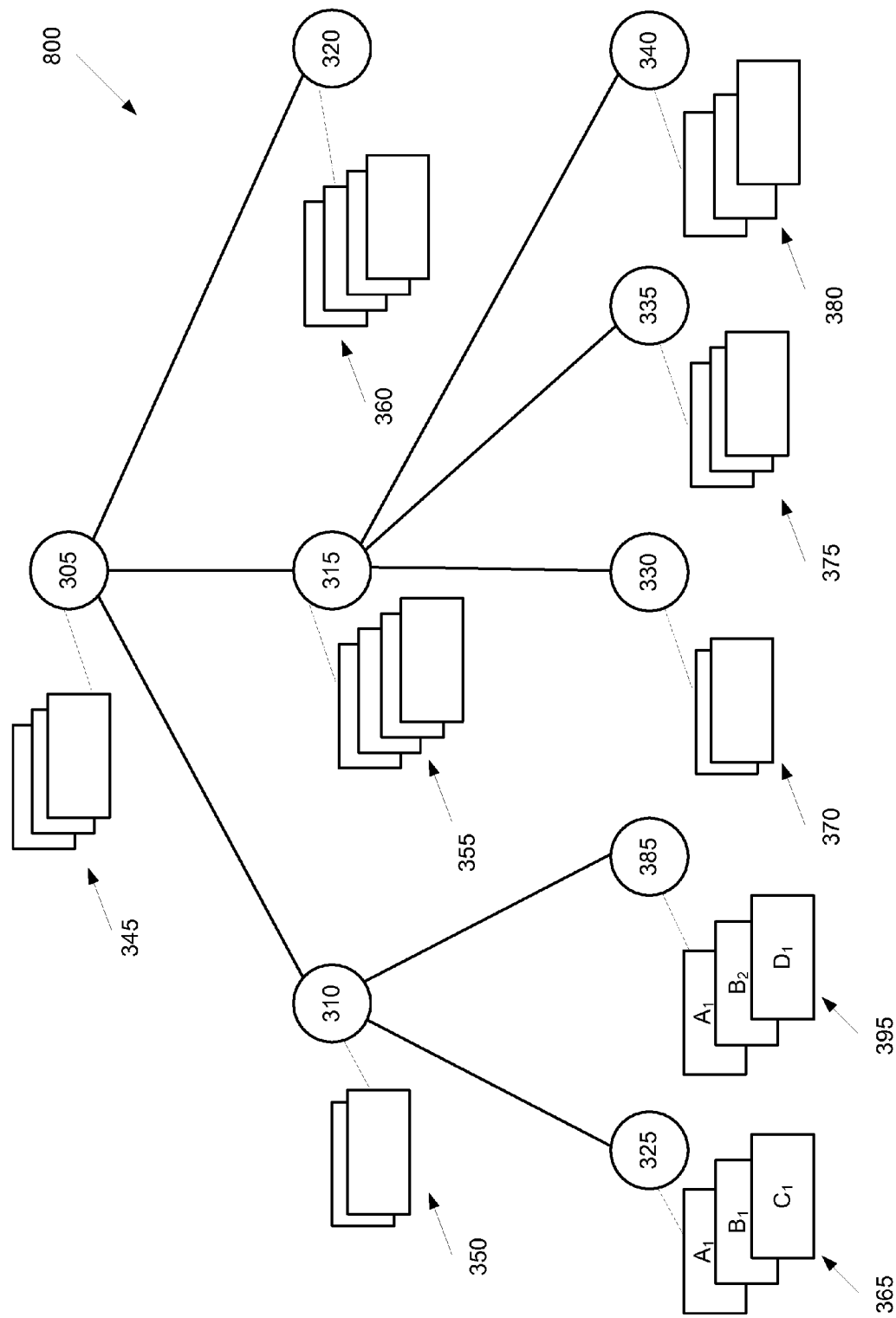
FIG. 8 illustrates a hierarchy of dashboards that provides an example of customizing a window within a dashboard.

FIG. 8 provides another hierarchy 800 of dashboards that illustrate another method of configuring a dashboard. This figure is similar to FIG. 7. However, in this example, the dashboard 385 is customized to include a different combination of panes. This is different from the example shown in FIG. 7 because a window pane has been replaced. Whereas, in the previous example, the window pane has not changed but only its view has changed. Therefore, the new dashboard 385 has three panes 395; two of which are the same as in the previous figure. However, instead of pane $C_1$, a different pane (i.e., pane $D_1$) is included in the dashboard 385. Similar to saving the view configuration, the new pane configuration can also be saved so that the user can use dashboard 385 for other patients.

As described further below, the user has the option of keeping the new dashboard private or allowing the other users to share and/or to modify it. The user can link the new dashboard to other dashboards in the hierarchy. For instance, a user might link the new dashboard 385 to dashboard 305. If dashboard 305 includes a summary list of patients, the user can link the new dashboard 385 to the name of one or more of the patients in dashboard 305 to display dashboard 385 upon selecting those patients in dashboard 305. In other words, the user can drill down to dashboard 385 directly from another dashboard several levels higher in the hierarchy.

Figure 9:
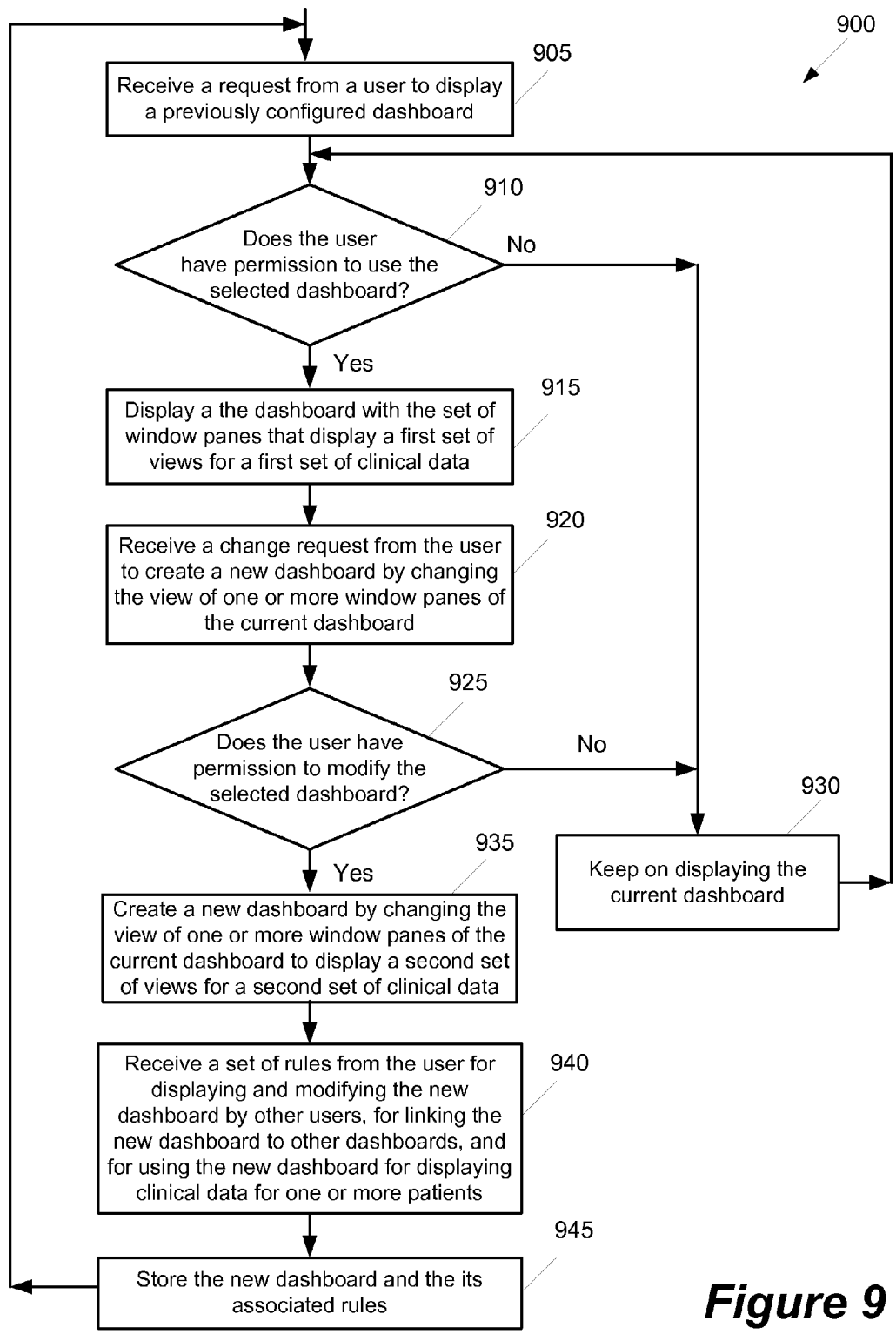
FIG. 9 conceptually illustrates a process for creating a new dashboard based on an existing dashboard by a user.

FIG. 9 conceptually illustrates a process 900 for creating a new dashboard based on an existing dashboard. As shown, the process receives (at 905) a request to display a previously configured dashboard. For instance, the user might have clicked on an item in the patient list window 505 in dashboard 500 that causes dashboard 600 to be displayed.

Figure 10:
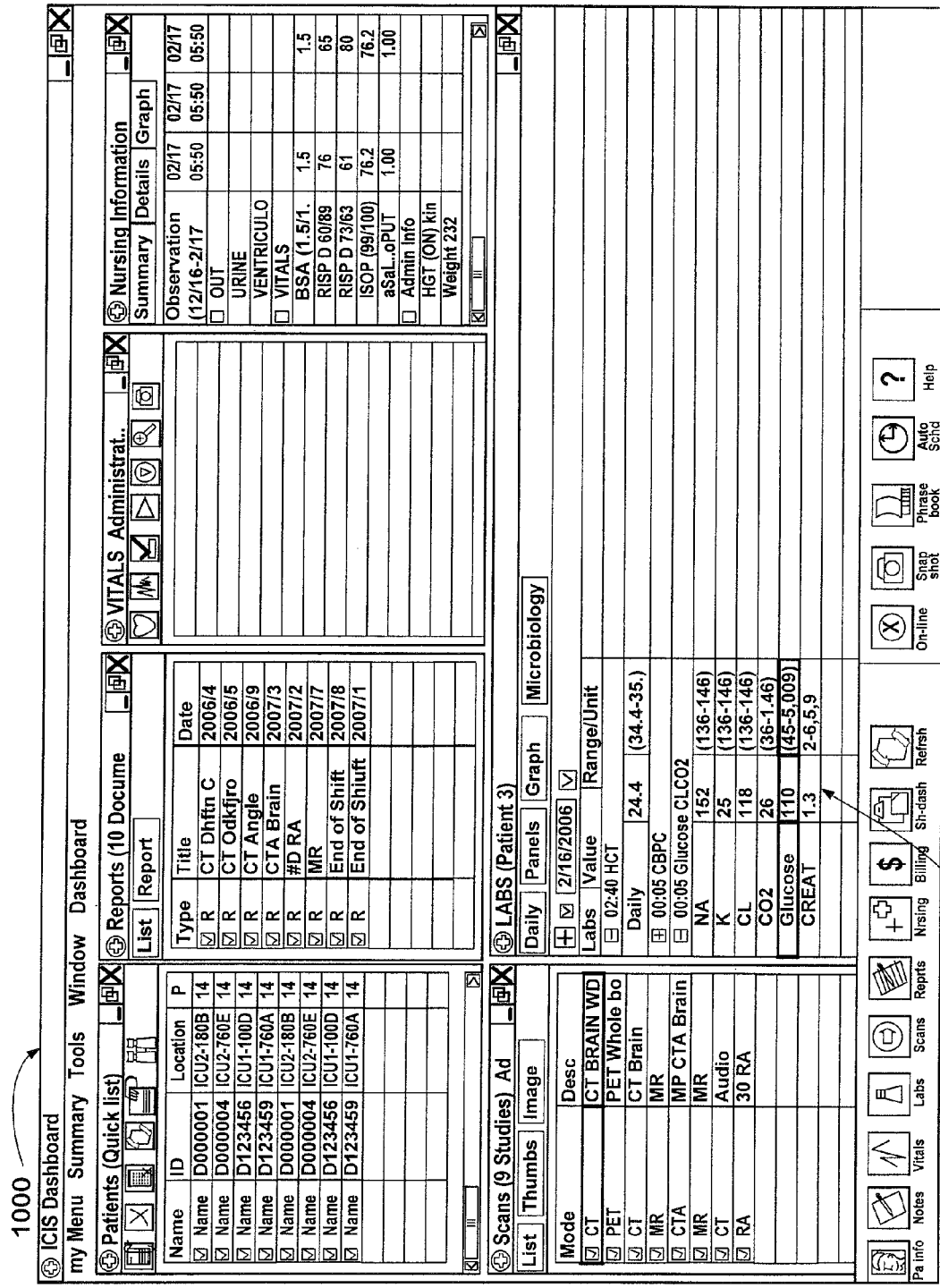
FIGS. 10-11 provides an illustrative example of customizing a view of a window in a dashboard.

Next, at 910, the process determines whether the user has permission to use the selected dashboard. When the user does not have permission to use the selected dashboard, the process (at 930) keeps displaying the current dashboard and proceeds to 910 which was described above. On the other hand, when the user has permission to use the selected dashboard, the process displays (at 915) the selected dashboard. FIG. 10 provides an illustrative example of a dashboard 1000 that is displayed when the user has permission. Specifically, dashboard 1000 contain several windows that includes the lab result window 1005.

Next, at 920, the process receives a request to create a new dashboard based on the current dashboard. The user can create this new dashboard by changing the view of one or more window panes of the current dashboard. For instance, the user might decide that instead of the list in the lab result window 1005, displaying a graph for glucose is more appropriate. The process determines (at 925) whether the user has permission to modify the selected dashboard. When the user does not have such permission, the process (at 930) keeps on displaying the current dashboard and proceeds to 910 which was described above.

Figure 11:
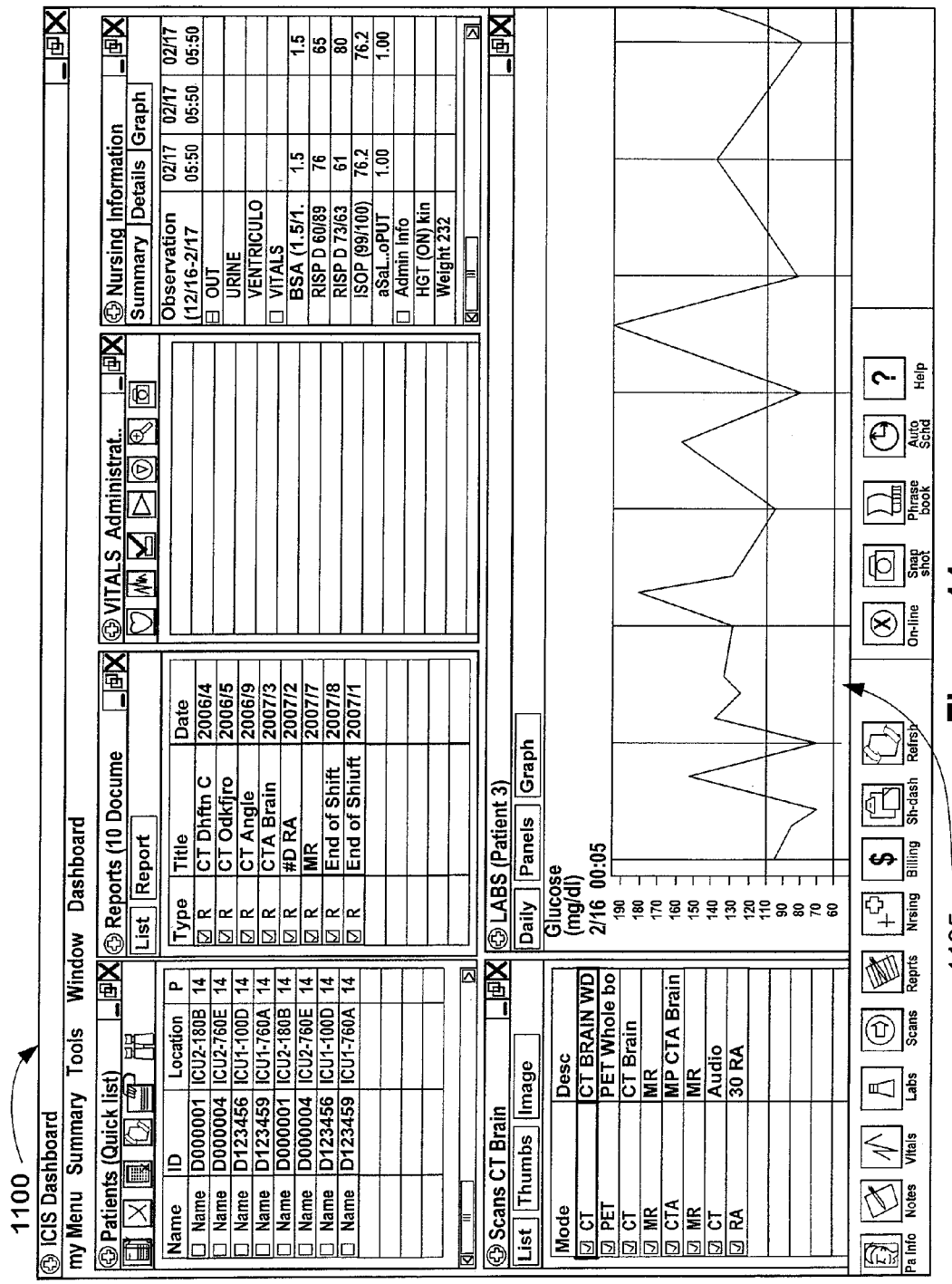

On the other hand, when the user has permission to modify the selected dashboard, the process creates (at 935) a new dashboard by making the requested change in the view of one or more window panes. FIG. 11 provides an illustrative example of a new dashboard 1100 which is created based on the existing dashboard 1000. As shown, in the dashboard 1100, the view of the window pane 1005 is changed from showing a list to showing a graph for glucose 1105. Next, at 940, the user optionally creates a set of rules to determine who can display or modify the new dashboard. The user can also determine for which patient or for which category of patients (e.g., diabetic patients) the new dashboard should be used. The user can also link the new dashboard to one or more other dashboards. For instance, the user can link dashboard 1100 to the name of a particular patient in the summary list to cause the new dashboard to be displayed when the name of that patient is selected by the user.

The user can also specify whether the new dashboard should be kept private or whether some other users can display the dashboard. The user can also give permission to some other users to further modify the dashboard. The user may link the new dashboard to other dashboards in the hierarchy. The user may also specify the new dashboard for showing clinical data for one or more patients.

Figure 12:
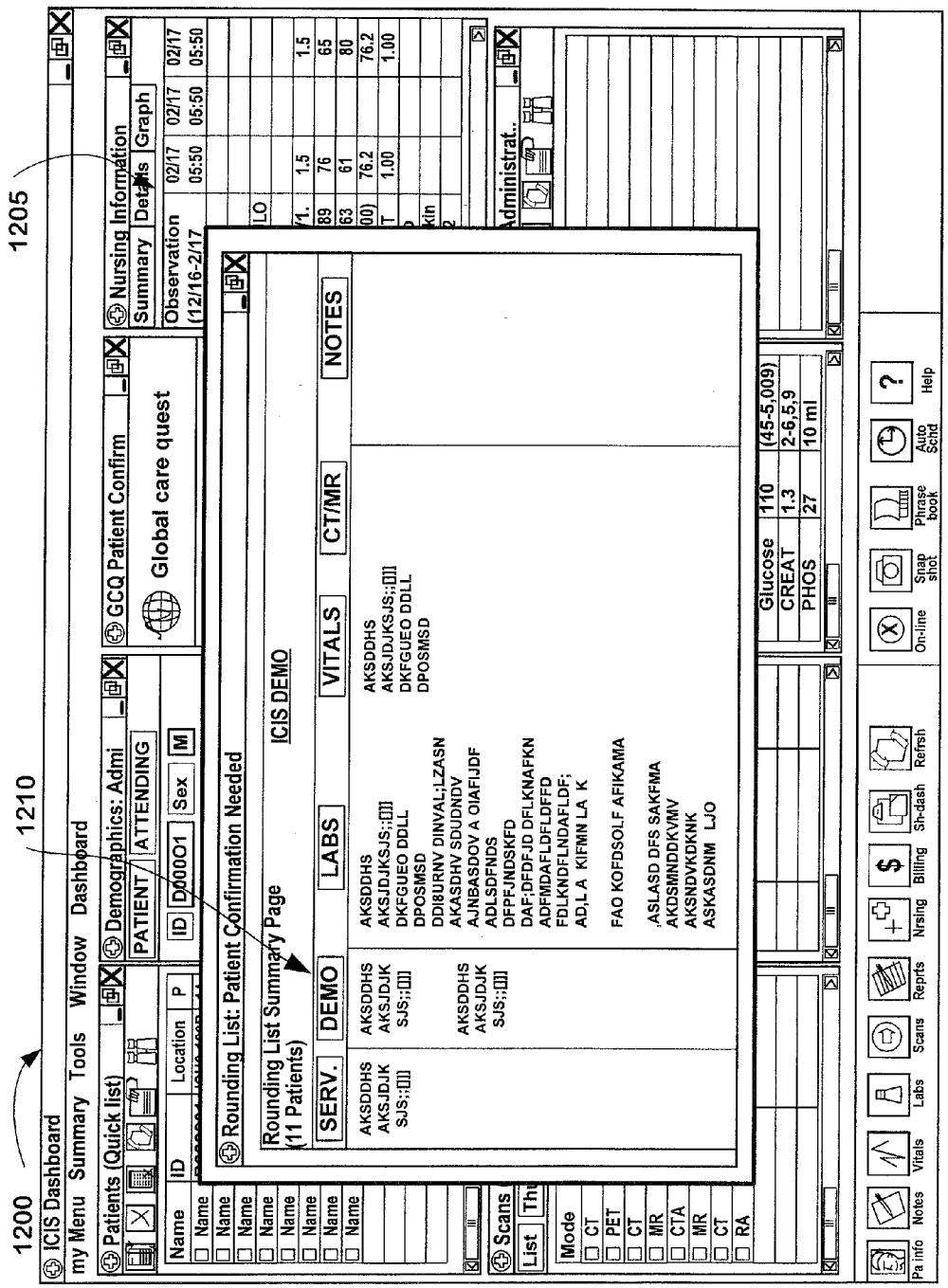
FIGS. 12-13 provides an illustrative example of displaying relevant information when a patient's condition is selected from a patient summary window.
Figure 13:
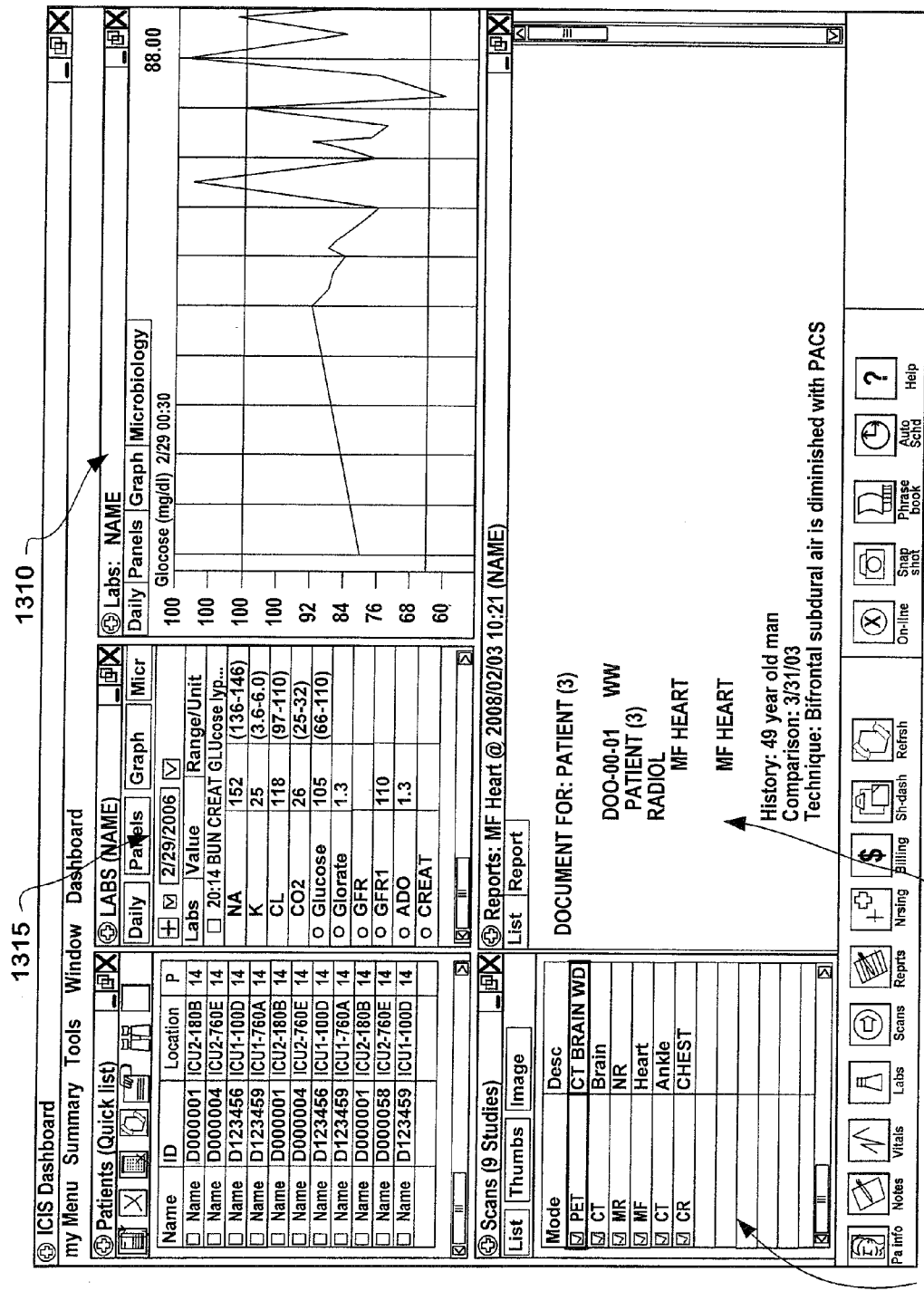

Next, at 945, the process stores the new dashboard and its associated rules for future use. Therefore, when treating a patient with a particular medical condition, the healthcare professional is initially presented with the most relevant information within a dashboard. FIGS. 12-13 provide an illustrative example of displaying a dashboard that drills down to most essential elements. As illustrated in FIG. 12, the user is first presented with a summary list 1205 for one or more patients. In some embodiments, the summary list is presented when a menu item in the menu bar is selected. The summary list 1205 includes a medical condition of the patient 1210. Also, the summary list may include other information such the patient's room number, MR number, PAD, attending name, service name, labs, vital ranges, list of operations (each with date, postoperative diagnosis, operation title, surgeon), impression part of most recent CXR, MRI scan, CT scan, latest nurse EOSS, 24 hour graphs (e.g., HR, RR, system BP, temperature, oxygen saturation, GCS, MEWS, Apache, SAPS, MAR), etc. In this example, the medical condition states that the patient is being treated for hyperglycemia.

When the medical condition 1210 is selected (e.g., by clicking on the item), the user is presented with dashboard 1300 as illustrated in FIG. 13. As illustrated, this dashboard includes (1) a report window 1305 that provides a detailed discussion of the patient's diagnosis, (2) glucose graph 1310 that provides information about the patient's glucose level, (3) lab results window 1315, and (4) scan window 1320. Therefore, through a single click of the patient's condition in the summary list 1205, the user is presented with a dashboard that contains relevant information. The goal being that once a condition is identified no additional selections are required to display the information that the user wants to view.

As an example, a selection of a patient name may open up a first dashboard related to the patient's admitting diagnosis and a selection of the medical condition may open up a second dashboard related to treating the medical condition. As discussed above, a dashboard may provide one or more links to other dashboards such as those that describe different protocols for treating a patient with such condition. For instance, when a user selects an item such as the condition in the summary window, the user can be presented with several dashboards instead of just one dashboard. For example, a dashboard related to patient's condition and a dashboard related to treating such condition may be presented when a user selects an item. More detailed information about drill-down dashboards can be found in U.S. patent application Ser. No. 12/036,281, filed on Feb. 24, 2008, and entitled "Drill Down clinical Information Dashboard." The contents of U.S. application Ser. No. 12/036,281 are herein incorporated by reference.

II. Overview of Single-Select Method for Launching Multiple Dashboards

Figure 14:
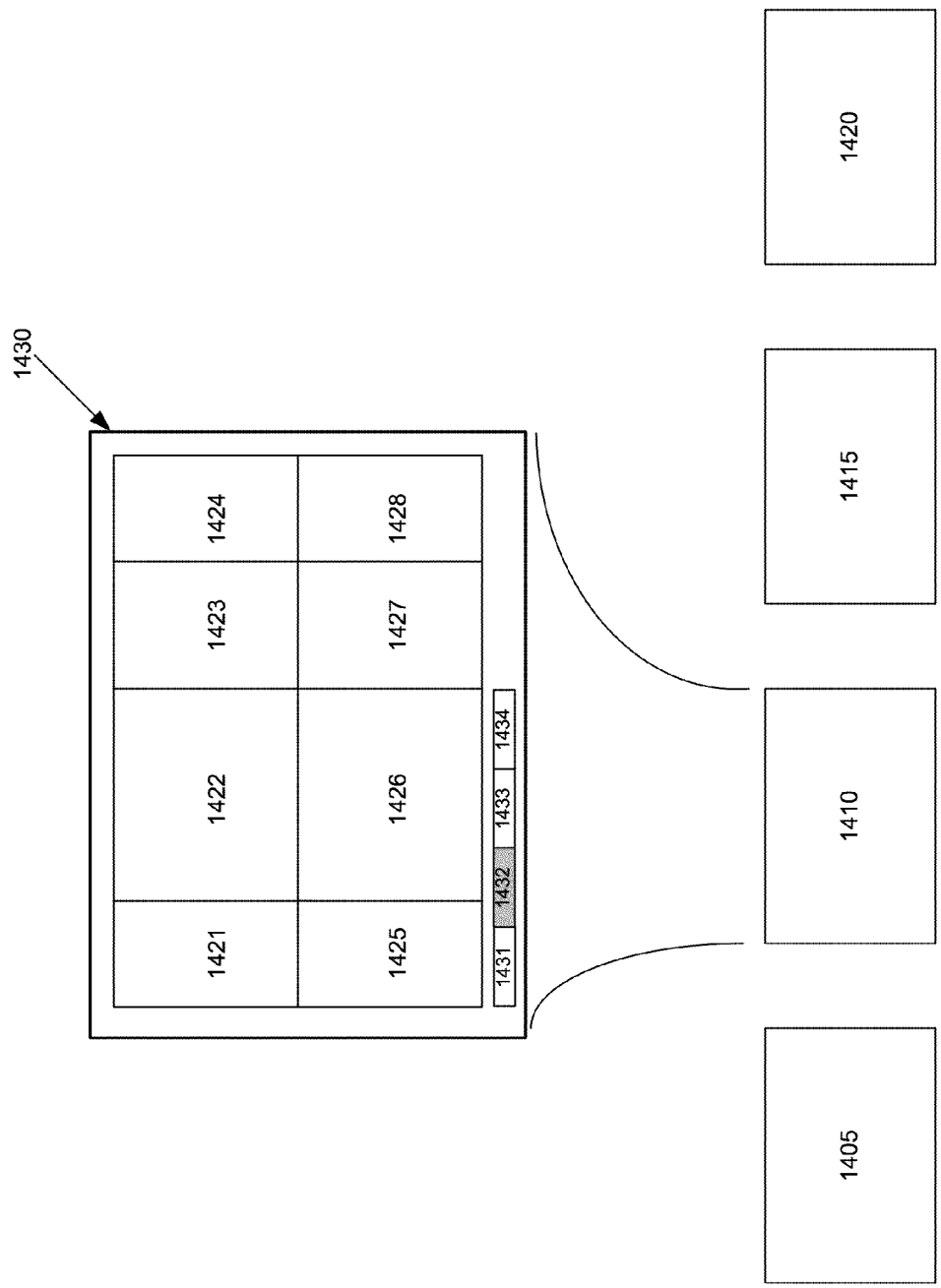
FIG. 14 provides an illustrative example of a set of dashboards that can be displayed in accordance with the inventive system and method.

As mentioned above, the method of some embodiments starts (also referred to as launches or instantiates) multiple dashboards based on the selection of a single piece of clinical information. For example, FIG. 14 illustrates multiple dashboards 1405, 1410, 1415, and 1420 that are launched by the selection of a single piece of clinical information. Dashboard 1410 is illustrated in expanded form, indicating that it is presently displayed on screen 1430. Dashboard 1410 includes eight window panes 1421-1428 that can be configured to provide information about a patient.

In some embodiments, one of the launched dashboards is displayed at its full resolution in a first display area of the display device, while the other launched dashboards are displayed as selectable icons (e.g., displayed as selectable thumbnails) in a second display area of the display device (e.g., in a display area below, above or to the side of the first display area, or in a display area overlapping the bottom, the top, the left or the right side of the first display area). Some of these embodiments also display a selectable icon in the second display area for the dashboard that is being displayed in the first display area. In FIG. 14, dashboard 1410 is displayed on the screen 1430 in a first display area, while icons 1431-1434 are displayed at the bottom of the screen in a second display area. Icon 1432 is highlighted indicating that dashboard 1410 (the second of the four dashboards) is presently displayed.

The selection of a selectable icon (e.g., a cursor click on the icon) in the second display area causes the display of the icon's associated dashboard in the first display area. In addition to this selection approach or in lieu of this approach, other embodiments use other techniques to display and navigate through the launched dashboards that are not being viewed at a particular time in the first display area. For instance, in the embodiments that display the dashboards on touch sensitive displays, some embodiments might allow a user to switch between the dashboards (i.e., to change the dashboard being displayed in the first display area) by swiping his hand over the display device in a particular direction (e.g., to the left or to the right). This swiping motion causes the first display area to switch from displaying a particular dashboard to one that is to the side of the particular dashboard that is opposite the direction of the swiping motion.

Given the large number of dashboards that are launched together, some embodiments allow a user (e.g., a doctor or other practitioner, a system administrator, etc.) to customize one or more window panes of a dashboard to display only a particular view of a particular clinical information piece (e.g., a 24 hr graph of glucose level). In some such embodiments, the user can optimize a dashboard to include several such parameters and view specific window panes that maximize the amount of data viewable at any given time and/or that group together clinical information views for quick deciphering and correlation by a practitioner. For instance, a left side of a dashboard could show several stack-aligned panes, each showing a vital statistic over a time period, while a right side of dashboard shows several stack-aligned panes, each showing a laboratory measurement over the same or different time period. Such parameter and data-intensive dashboard can be printed or e-mailed for providing practitioners detailed snapshots of a patient's condition at a particular time. The use of the parameters and view-specific dashboards is not limited to embodiments that launch multiple dashboards at once.

Figure 15:
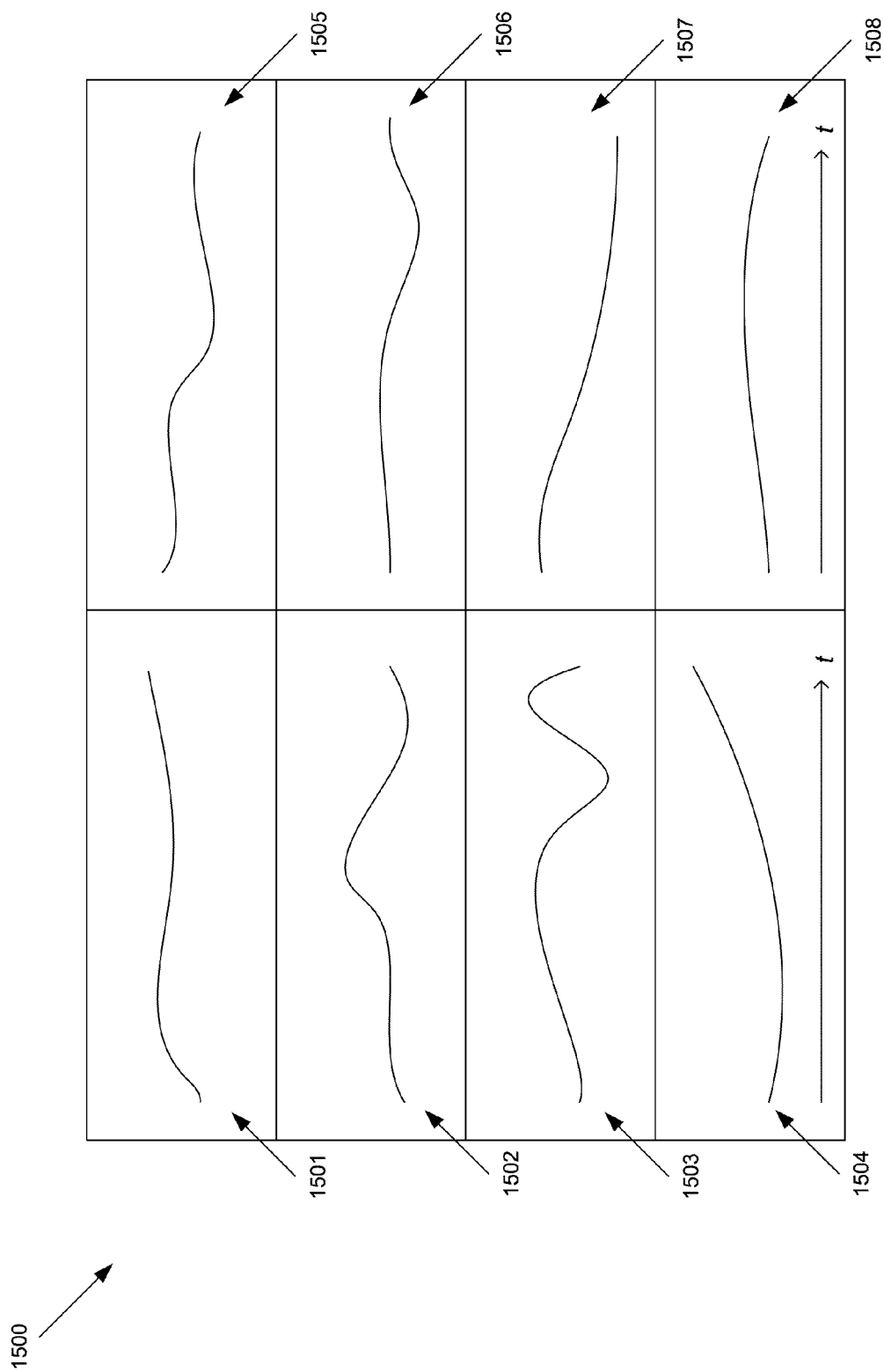
FIG. 15 illustrates a dashboard with window panes in accordance with some embodiments of the present invention.

FIG. 15 illustrates a dashboard 1500 with window panes 1501-1508. Each of the window panes 1501-1508 is a plot of the values of a particular parameter over a specified amount of time. For example, window panes 1501-1504 (the left column) might be a vital signs (e.g., heart rate, blood pressure, etc.) while window panes 1505-1508 might be labs (e.g., blood glucose, white blood cell count, etc.). Other embodiments might display other stacked trend graphs.

Because several window panes of a dashboard can be parameter-specific, some embodiments define a data element to represent each parameter that is presented in each parameter-specific window. For instance, assume that a dashboard has three specific window panes showing different views of a particular measurement value. One showing a running twenty-four hour graph of a particular measurement value, one showing the running twenty-four hour graph of the average of the particular measurement value, and one showing the running twenty-four hour graph of the variability coefficient associated with the change of the particular measurement value. Some embodiments would define a different data element to keep track of each of the values displayed in each of these three window panes, even though they all relate from the same measurement value. These embodiments define these data elements so that different mathematical functions and display views can be defined for each of them. The use of the data-element model is not limited to the embodiments that use parameter- and view-specific panes.

Some embodiments provide several software tools to allow a user to design a dashboard. For instance, some tools allow the user to specificity the number of panes in a dashboard, to select among different layout types for a particular number of panes, to move and adjust window panes in a dashboard that is from a selected dashboard layout, etc. Some embodiments allow a user to tie a window pane to a particular view of a particular parameter. For instance, in some embodiments, the user can (1) right-hand click on a window pane in a dashboard, (2) select vital signs instead of lab measurements in a menu that is displayed in a resulting menu, (3) select heart rate in a resulting drop down menu of vital sign, and then (4) select a particular view (e.g., running twenty-four hour view) of the heart rate. The software tools of some embodiments allow the user to move and resize the window panes so that the user can create aligned and/or condensed parameter- and view-specific panes in order to maximize the amount of data being viewed and/or to simplify the correlation of such data.

Each dashboard launched by the single-select method of some embodiments is a single "flat" dashboard that cannot be "drilled down" to another dashboard. In other embodiments, each launched dashboard can be a drill-down dashboard, i.e., a dashboard that is several dashboards that are linked together so that a user can navigate between them by selecting items displayed in the dashboards (e.g., by traversing from a first dashboard to a second dashboard through a selection of an item in a window pane of the first dashboard). In other words, some embodiments use the single-select method of some embodiments in lieu of drilldown dashboards, while other embodiments use the single-select method in conjunction with drill-down dashboards.

III. Single-Select Method for Launching Multiple Dashboards

A. Launching and Navigating Multiple Dashboards

Some embodiments provide a user interface tool for configuring multiple dashboards that can be accessed by a single selection of a piece of clinical information. For instance multiple dashboards are accessed by selecting a single patient from a patient list (e.g., by clicking on the patient's name) or by selecting a condition from a condition list. A patient list in some embodiments is a list of a doctor's current patients displayed on a screen. Clicking on the patient would allow the doctor to access multiple dashboards that are preconfigured.

In some embodiments, the doctor (or another user) has pre-configured dashboards based on patient conditions. For example, selecting a patient with a brain tumor brings up a set of dashboards specifically designed for patients with brain tumors in some embodiments. Such a set of dashboards has information that a doctor would typically want to see when examining such a patient. In some embodiments, a doctor can print one or more of the dashboards in the set to use when examining the patient.

Some embodiments include different numbers of window panes in a dashboard, and some embodiments have dashboards with different setups. In some embodiments, each of the multiple dashboards can be configured to have any number of window panes, while some embodiments limit the number of window panes per dashboard to eight. Other embodiments can provide different limits on the number of window panes. In some embodiments, each of the multiple dashboards can be configured such that each dashboard provides different information about the patient.

Figure 16:
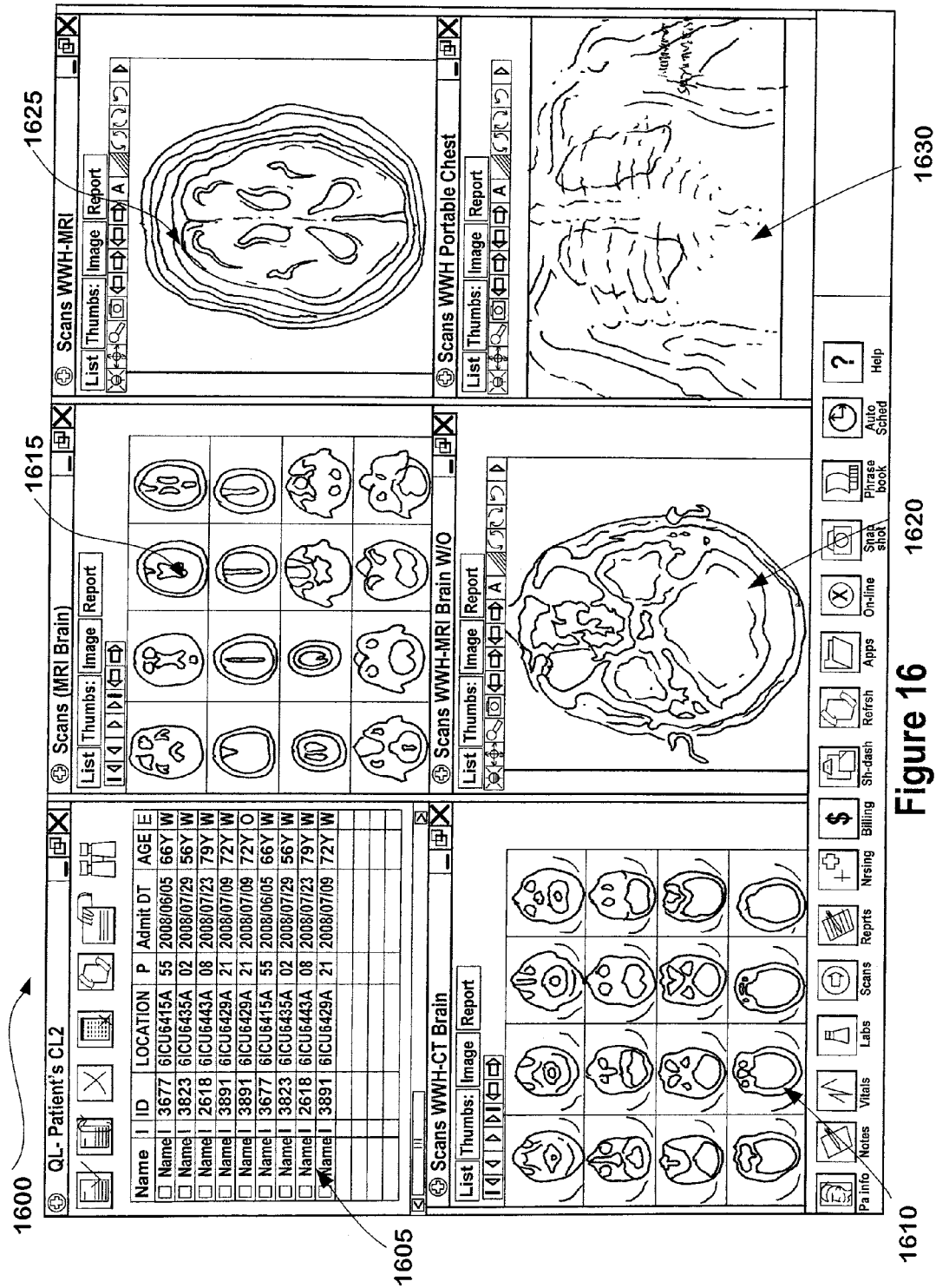
FIG. 16 illustrates a dashboard in accordance with some embodiments of the present invention that is launched by the selection of a single patient from a patient list.
Figure 17:
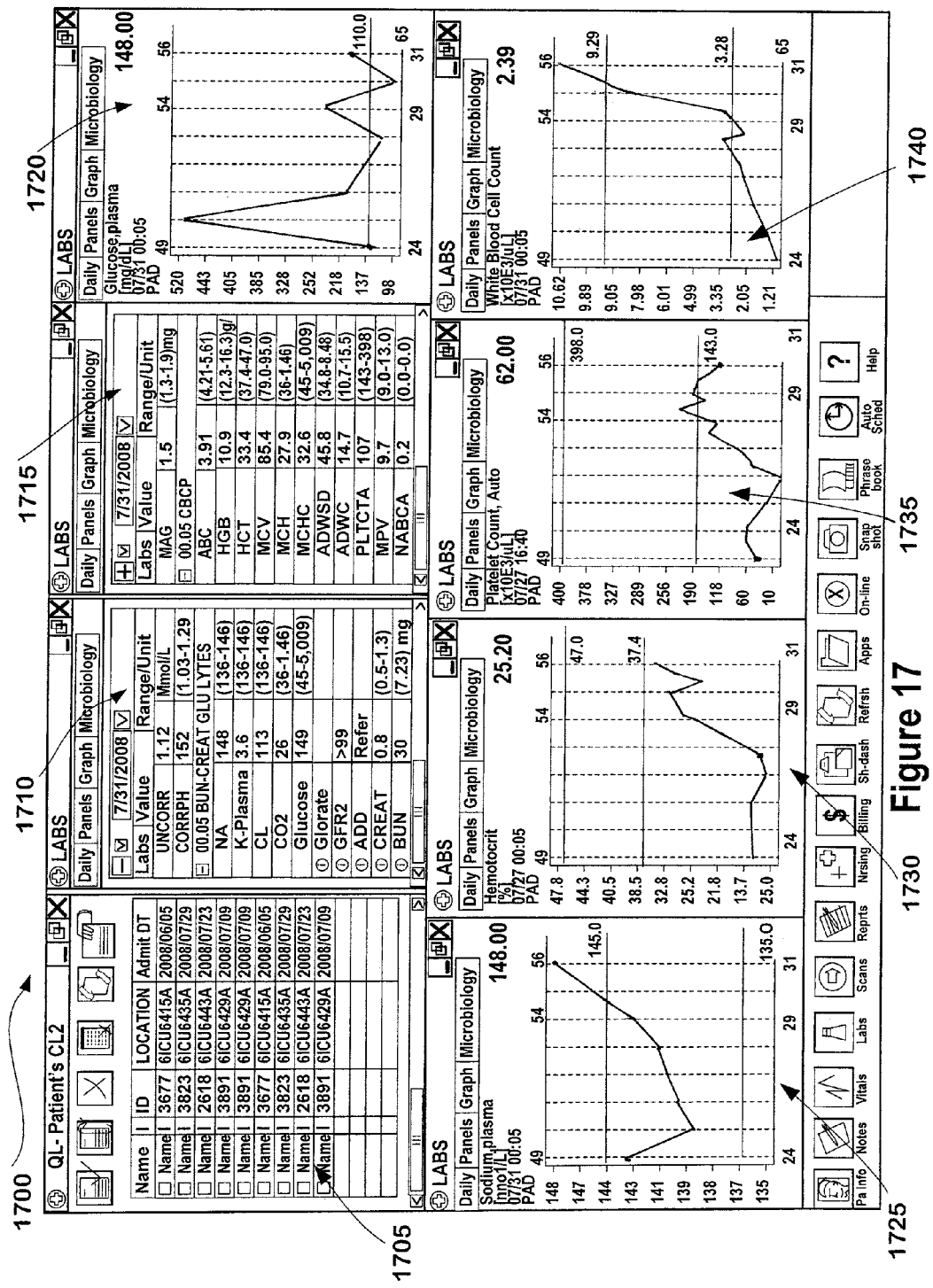
FIG. 17 illustrates a dashboard in accordance with some embodiments of the present invention that is launched by the selection of a single patient from a patient list.
Figure 18:
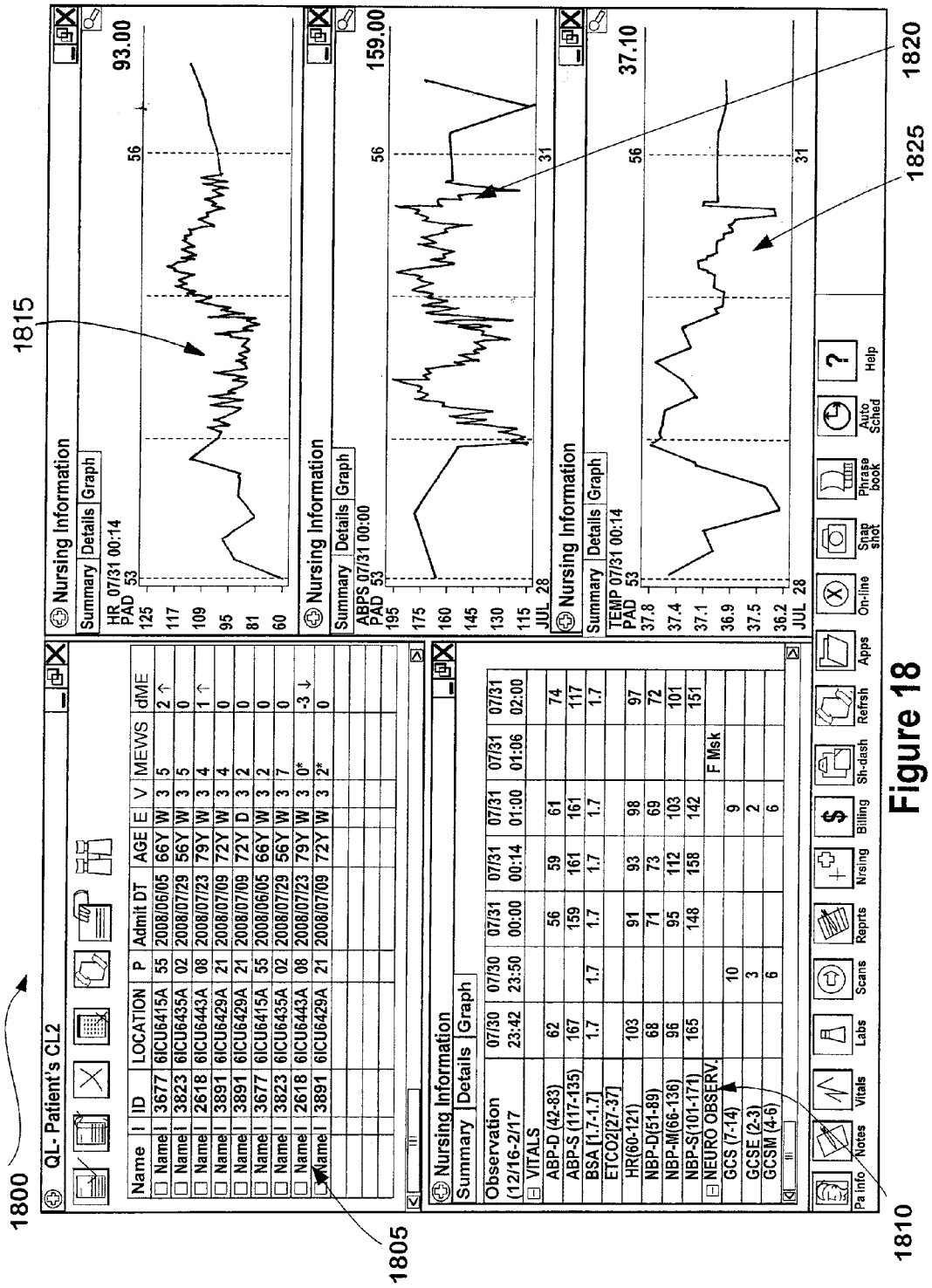
FIG. 18 illustrates a dashboard in accordance with some embodiments of the present invention that is launched by the selection of a single patient from a patient list.

For example, FIGS. 16-18 illustrate multiple dashboards of some embodiments that are launched by the selection of a single patient from a patient list. Each of the dashboards is configured to present different information with differently shaped and sized panes. Selecting a single patient launches a scans dashboard 1600, a labs dashboard 1700, and a nursing dashboard. Some embodiments also launch other dashboards (e.g., a vitals dashboard showing vital signs). The scans dashboard includes six window panes 1605-1630: a patient list 1605, two thumbnails of brain scans 1610 and 1620, two large brain scans 1615 and 1625, and a chest x-ray 1630. The labs dashboard 1700 includes eight window panes 1705-1740: a patient list 1705, two summary windows 1710 and 1715, and four trend graphs of specific labs 1720-1740. The nursing dashboard 1800 includes only five window panes: a patient list 1805, a nursing summary 1810, and three trend graphs 1815-1825.

Some embodiments display one of the multiple dashboards at a time, and allow the user to scroll through the various dashboards. For example, referring back to FIG. 14 above, when dashboard 1410 is selected, that dashboard would take up most of the user's screen, while buttons to select dashboards 1405, 1415, and 1420 would be available at the bottom of the screen in some embodiments. Other embodiments might display selection buttons for the non-displayed dashboards elsewhere on the screen. Some embodiments allow a user to scroll through the dashboard with touch gestures. For example, in some embodiments a user can make a sweeping gesture across a touch-sensitive device (either a screen, a touchpad, or other such device) to indicate to move to a previous or next dashboard. In the example in which dashboard 1410 is displayed, making a sweeping gesture from right to left would "sweep" dashboard 1410 off the screen to the left and display dashboard 1415 in some embodiments.

B. Parameter-Specific Window Panes

In some embodiments, the various window panes in a dashboard display parameters with no other elements in the window pane. Some embodiments maximize space and create a data intensive interface by eliminating borders and controls from the window panes. A displayed parameter could be, for example, the patient's white blood cell count or the patient's blood glucose level. In some embodiments, a single window pane displays a single data element about a specific parameter. For example, a single window pane can display the current information about a patient's heart rate. However, often of more use to a doctor is a graph of the patient's heart rate over the past 24 hours (or some other length of time). Other embodiments provide other data elements that can be displayed for specific parameters. For example, some embodiments display a graph of the value of the parameter for the previous 24 hours (or other length of time), a 24 hour (or other length of time) average, a display of the minimum and maximum values (over some specified length of time) along with the current value, a variability coefficient that illustrates how much the parameter has changed over a specified length of time (i.e., whether the parameter has been fairly constant or has bounced up and down substantially over the specified length of time), or a variation from a specified ideal value for the parameter (e.g., how far and in what direction the patient's heart rate varies from an ideal of 70 beats per minute).

Figure 19:
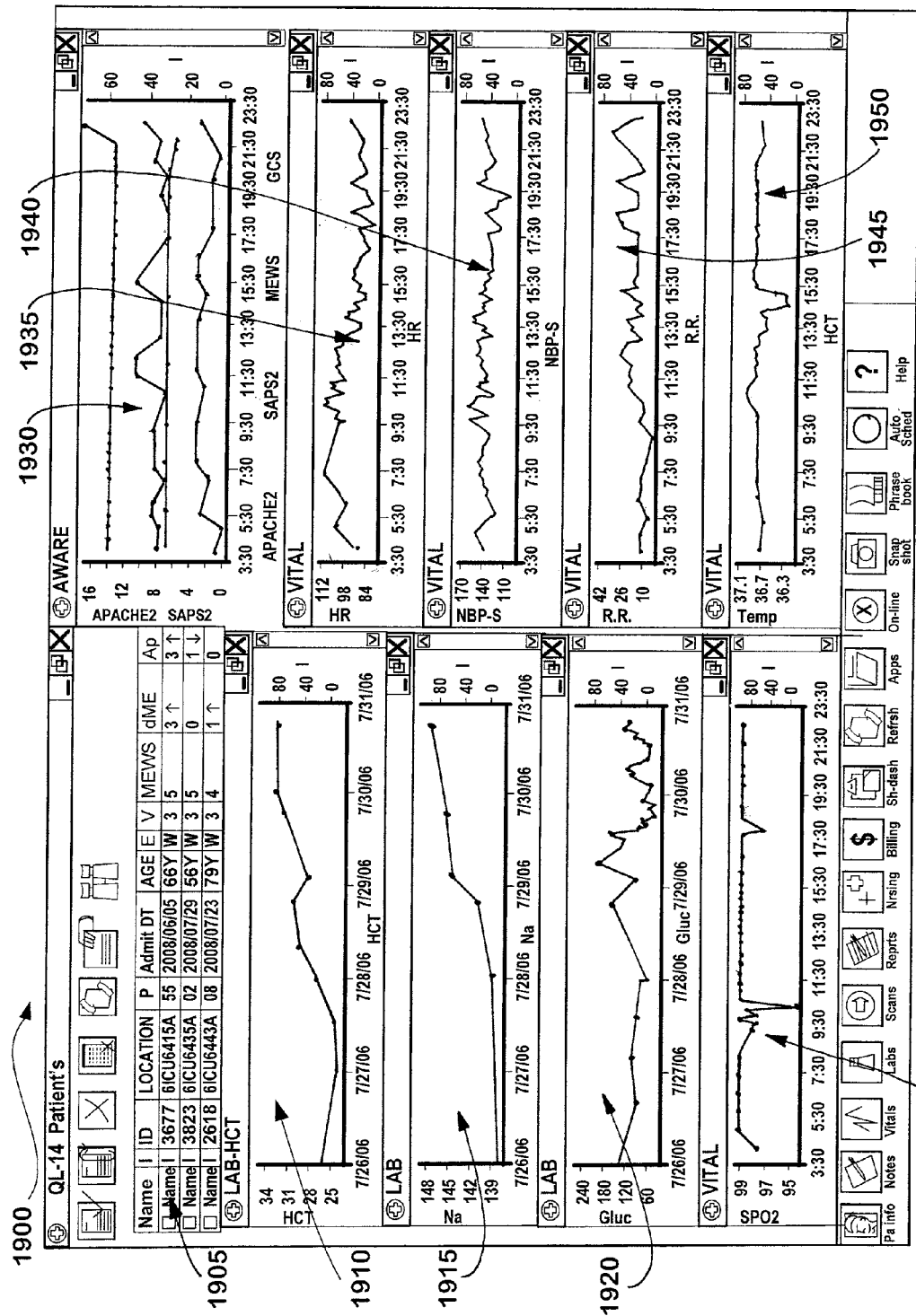
FIG. 19 illustrates a dashboard in accordance with some embodiments of the present invention wherein the dashboard display a plurality of stacked trend graphs.

In some embodiments the window panes within a dashboard are optimized to provide the most amount of useful data to a physician. For example, rather than simply seeing one parameter, a physician might want to look at the trends of multiple parameters over the same length of time. FIG. 19 illustrates a dashboard 1900 with stacked trend graphs. Each of the window panes 1910-1950 in dashboard 1900 includes a trend graph for a single parameter, with minimal controls or borders so as to maximize the use of screen space (compare, for example, to the window panes of dashboard 1800). Each of the vitals trend graphs (window panes 1925 and 1935-1950) and the severity score trend graphs (window pane 1930) shows the value of the vital sign over the past 24 hours, while the labs trend graphs show the value of the labs over the past 5 days.

C. Configuring Multiple Dashboards

As mentioned above, some embodiments provide a user interface tool that allows a user to configure a set of dashboards. In some embodiments of the user interface tool, a user first determines what will prompt the dashboard set (e.g., what patient condition will prompt the dashboard set). Next a user selects a layout for a first dashboard (e.g., eight square window panes, etc.). In some embodiments the layout can be modified by dragging the edges of the window panes.

Next, the user selects a window pane and chooses a menu to determine the parameter for the menu. In some embodiments, the menus include vital signs, labs, images (e.g. x-rays), and other options. Once the user has selected a menu, the user then selects a parameter in some embodiments. For example, the vital sign menu might include the parameters heart rate, blood pressure, breathing rate, etc. Once the user has selected a parameter, the user is then presented with a menu of data elements that can be displayed about the parameter. For example, as described above, the different data element choices might be a graph of the trend over a particular length of time, a minimum and maximum value over a particular length of time, a running average over a particular length of time, the variability coefficient of the parameter, or a graph showing the variation from an ideal value for the parameter.

Once a user has configured the first window pane, the user can then configure the other window panes for the first dashboard in the same way. After configuring all the window panes in the first dashboard, the user can then configure the other dashboards in the set in the same manner that they configured the first dashboard.

Figure 20:
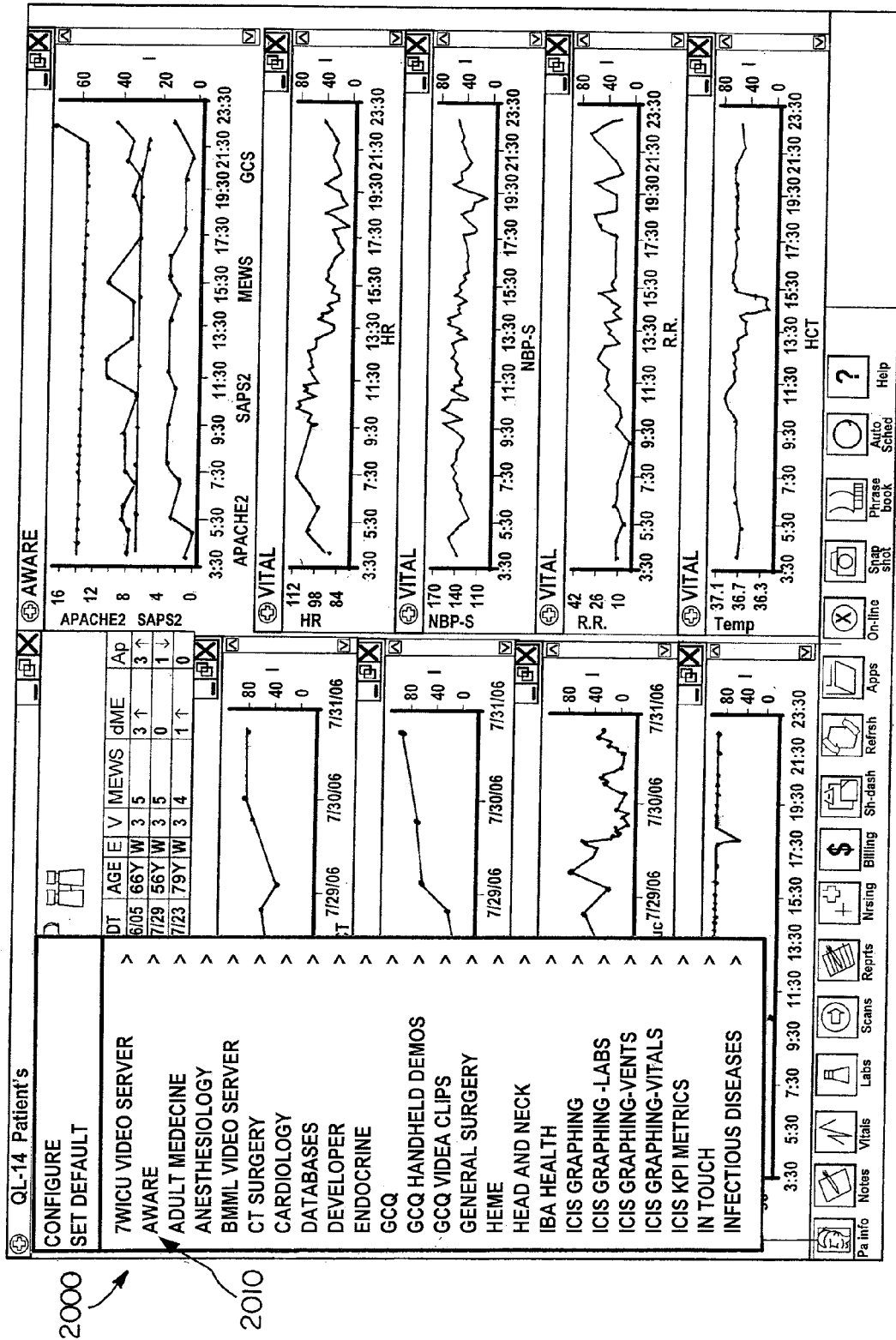
FIG. 20 illustrates a user configuring a window pane of a dashboard in accordance with one embodiment of the present invention.

FIG. 20 illustrates a user configuring a window pane of a dashboard. In some embodiments, after selecting a window pane (e.g., pane 2005), a user can bring up a set of options for that window pane. Menu 2010 illustrates different categories (e.g., cardiology, endocrine, etc.) which a user can select to bring up other options for the windowpane, as described above. Other embodiments bring up a menu like menu 2010 by right-clicking in the window pane. In some embodiments, a menu similar to menu 2010 can be accessed in order for a user to switch to a completely different preconfigured dashboard.

IV. Computer System

Figure 21:
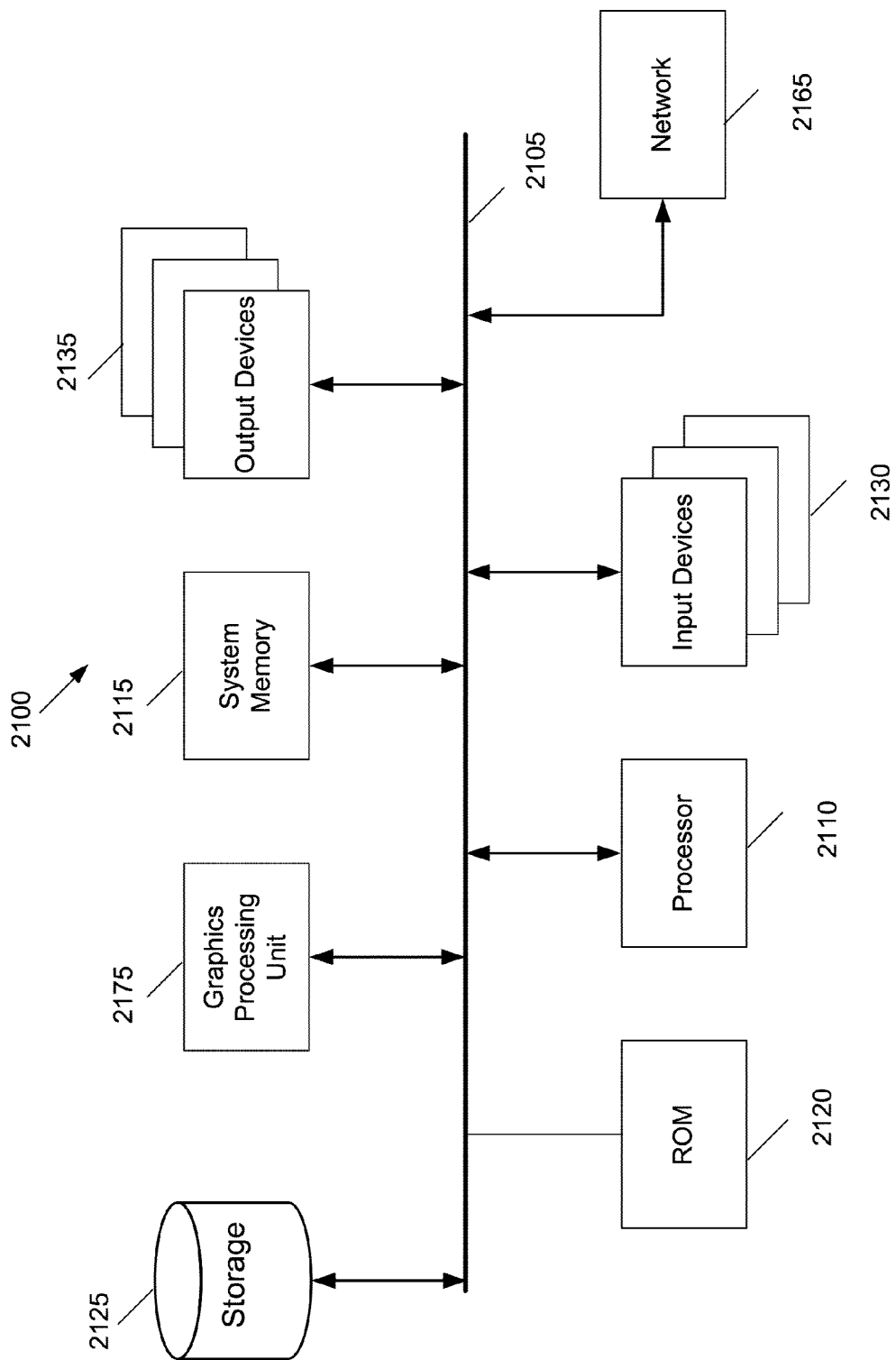
FIG. 21 conceptually illustrates a computer system with which some embodiments of the invention are implemented.

FIG. 21 conceptually illustrates a computer system with which some embodiments of the invention are implemented. The computer system 2100 includes a bus 2105, a processor 2110, a system memory 2115, a read-only memory 2120, a permanent storage device 2125, input devices 2130, and output devices 2135. In some embodiments, the computer system also includes a graphic processing unit (GPD) 2175.

The bus 2105 collectively represents all system, peripheral, and chipset buses that support communication among internal devices of the computer system 2100. For instance, the bus 2105 communicatively connects the processor 2110 with the read-only memory 2120, the system memory 2115, and the permanent storage device 2125.

From these various memory units, the processor 2110 (also referred to as central processing unit or CPU) retrieves instructions to execute and data to process in order to execute the processes of the invention. The read-only-memory (ROM) 2120 stores static data and instructions that are needed by the processor 2110 and other modules of the computer system.

The permanent storage device 2125, on the other hand, is a read-and-write memory device. This device is a non-volatile memory unit that stores instruction and data even when the computer system 2100 is off. Some embodiments of the invention use a mass-storage device (such as a magnetic or optical disk and its corresponding disk drive) as the permanent storage device 2125.

Other embodiments use a removable storage device (such as a floppy disk or Zip® disk, and its corresponding disk drive) as the permanent storage device. Like the permanent storage device 2125, the system memory 2115 is a read and write memory device. However, unlike storage device 2125, the system memory is a volatile read-and-write memory, such as a random access memory. The system memory stores some of the instructions and data that the processor needs at runtime.

Instructions and/or data needed to perform processes of some embodiments are stored in the system memory 2115, the permanent storage device 2125, the read-only memory 2120, or any combination of the three. For example, the various memory units may contain instructions for processing multimedia items in accordance with some embodiments. From these various memory units, the processor 2110 retrieves instructions to execute and data to process in order to execute the processes of some embodiments.

The bus 2105 also connects to the input and output devices 2130 and 2135. The input devices enable the user to communicate information and select commands to the computer system. The input devices 2130 include alphanumeric keyboards, touch panels, and cursor controllers. The input devices 2130 also include scanners through which an image can be input to the computer system. The output devices 2135 display images generated by the computer system. For instance, these devices display IC design layouts. The output devices include printers, pen plotters, laser printers, ink-jet plotters, film recorders, and display devices, such as cathode ray tubes (CRT), liquid crystal displays (LCD), or electroluminescent displays.

Also, as shown in FIG. 21, bus 2105 also couples computer 2100 to a network 2165 through a network adapter (not shown). In this manner, the computer can be a part of a network of computers (such as a local area network ("LAN"), a wide area network ("WAN"), or an Intranet) or a network of networks (such as the Internet). Finally, as shown in FIG. 21, the computer system in some embodiments also optionally includes a graphics processing unit (GPU) 2175. A GPU (also referred to as a visual processing unit or a display processor) is a dedicated graphics rendering device which is very efficient in manipulating and displaying computer graphics. The GPU can be included in a video card (not shown) or can be integrated into the mother board of the computer system along with the processor 2110. Also, the computer system 2100 may be used as a personal computer, a workstation, a game console, or the like. Any or all of the components of computer system 2100 may be used in conjunction with the invention. However, one of ordinary skill in the art will appreciate that any other system configuration may also be used in conjunction with the invention.

While the invention has been described with reference to numerous specific details, one of ordinary skill in the art will recognize that the invention can be embodied in other specific forms without departing from the spirit of the invention. In other places, various changes may be made, and equivalents may be substituted for elements described without departing from the true scope of the present invention. For instance, while several example dashboards have been shown as a part of a multi-document interface (MDI), one ordinary skill in the art will recognized that the dashboard can be provided as a group of panes without a parent window. One of ordinary skill in the art will also realize that the dashboards can be displayed on a variety of interface devices in a variety of embodiments, e.g. computer displays, PDAs, cell phones, etc.

What is claimed is:

1. A system for presenting clinical information including medical data, the system comprising:
   a computer system;
   a user interface in communication with said computer system;
   software executing on said computer system for displaying a first component of clinical information on said interface;
   software executing on said computer system for launching a plurality of dashboards in response to a selection of said first component of clinical information, the plurality of dashboards having a first dashboard having a predefined configuration based upon a selected user profile;
   software executing on said computer system for displaying a selectable icon for each of said plurality of dashboards, wherein a selection of a particular icon causes the display of the dashboard associated with the particular icon;
   software executing on the computer system for displaying at least one of said dashboards in a first display area of said interface prior to the selection of any of the plurality of icons;
   software executing on said computer system for displaying a second dashboard in said first display area in response to a selection of the icon associated with said second dashboard,
   wherein said plurality of icons are displayed in a second display area, and wherein said plurality of icons are used for a multi-stage procedure.

2. The system of claim 1, wherein the second display area overlaps the first display area.

3. The system of claim 1, wherein the second display area is adjacent to said first display area.

4. The system of claim 1, wherein one said dashboard displayed in the first display area is displayed at a high resolution, while the icons in the second display area are displayed as low resolution representations of the dashboards.

5. The system of claim 1, wherein said plurality of dashboards do not comprise a drill-down dashboard or a component a drill down dashboard.

6. The system of claim 1, wherein at least one of said plurality of dashboards is not a drill-down dashboard or a component of a drill down dashboard.

7. The system of claim 1, further comprising:
   software executing on said computer system for displaying a mechanism on said interface for navigating through said plurality of launched dashboards.

8. A method for presenting clinical information including medical data, the method comprising the steps of:
   displaying a first component of clinical information;
   receiving a selection of said first component of clinical information;
   launching a plurality of dashboards in response to said selection;
   displaying a selectable icon for each of said plurality of dashboards,
   displaying a dashboard associated with a selectable icon in response to a selection of the icon,
   displaying at least one of said dashboards in a first display area prior to the selection of any of the plurality of icons,
   wherein displaying said plurality of icons comprises displaying said plurality of icons in a second display area,
   wherein the plurality of dashboards has a first dashboard having a predefined configuration based upon a selected user profiles, and
   wherein said plurality of icons are used for a multi-stage procedure.

9. The method of claim 8, further comprising:
   software executing on said computer system for displaying a second dashboard in said first display area in response to a selection of the icon associated with said second dashboard.

10. The method of claim 9, wherein a dashboard displayed in the first display area is displayed at a high resolution, while the icons displayed in the second display area are low resolution representations of the dashboards.

11. The method of claim 8, wherein said plurality of dashboards do not comprise a drill-down dashboard or a component of a drill down dashboard.

12. The method of claim 8, wherein at least one of said plurality of dashboards is not a drill-down dashboard or a component of a drill down dashboard.

13. A method for presenting clinical information including medical data, the method comprising the steps of:
   receiving a patient list;
   selecting a single patient from a patient list;
   launching multiple dashboards in response to said selection of said single patient from said patient list, each dashboard comprising a set of window panes, each window pane for providing at least one view of clinical information including medical data related to said single patient, wherein the multiple dashboards have a predefined configuration based upon a selected user profile; and
   providing a mechanism outside of the window panes of the dashboards for navigating through the launched dashboards.

14. The method of claim 13, further comprising:
   displaying one of the launched dashboards in a first display area;
   wherein providing the mechanism comprises providing a mechanism to switch the dashboards displayed in the first display area.

15. The method of claim 14, wherein providing the mechanism to switch the dashboards comprises providing a set of user interface tools to allow a user to switch the dashboards displayed in the first display area.

16. The method of claim of claim 15, wherein the set of user interface tools comprises a plurality of icons, each of said plurality of icons representing one of the launched dashboards.

17. The method of claim 15, wherein the set of user interface tools includes a plurality of icons, each icon representing one of the launched dashboards.

18. A method of configuring a clinical information display for medical data comprising a dashboard, the dashboard comprising a set of window panes for providing information about a first set of medical parameters, each parameter representing an aspect of a patient's condition, the method comprising the steps of:

receiving a selection of a type of events that trigger a display of the dashboard;

receiving a selection of a layout of the dashboard, the layout comprising a number of the window panes and an arrangement of the window panes on the dashboard;

for each window pane in said layout, selecting a particular parameter for display in the window pane, wherein each window pane is parameter-specific;

for each parameter selected for a window pane, receiving a selection of a data element for displaying the parameter; and storing said layout of the dashboard, wherein a data element is one of a graph trend over a particular length of time, minimum and maximum value over a particular length of time, a running average over a particular length of time, a variability coefficient of a parameter, and a graph showing a variation from an ideal value of a parameter, wherein the parameter is one of a vital sign and an element of a lab report, and wherein said selection of a type of events that trigger a display of the dashboard includes selecting a single patient from a patient list.

* * * * *